(12) United States Patent
Mace et al.

(10) Patent No.: US 12,115,471 B2
(45) Date of Patent: Oct. 15, 2024

(54) AQUEOUS TWO-PHASE SYSTEM FOR THE SEPARATION AND RECOVERY OF MAMMALIAN CELLS FROM CONTAMINATED CULTURES

(71) Applicant: Trustees of Tufts College, Medford, MA (US)

(72) Inventors: Charles R. Mace, Medford, MA (US); Christopher Luby, Medford, MA (US)

(73) Assignee: Trustees of Tufts College, Medford, MA (US)

( * ) Notice: Subject to any disclaimer, the term of this patent is extended or adjusted under 35 U.S.C. 154(b) by 1262 days.

(21) Appl. No.: 16/624,867

(22) PCT Filed: Jul. 3, 2018

(86) PCT No.: PCT/US2018/040724
§ 371 (c)(1),
(2) Date: Dec. 19, 2019

(87) PCT Pub. No.: WO2019/010186
PCT Pub. Date: Jan. 10, 2019

(65) Prior Publication Data
US 2020/0129886 A1 Apr. 30, 2020

Related U.S. Application Data

(60) Provisional application No. 62/528,209, filed on Jul. 3, 2017.

(51) Int. Cl.
*B01D 21/26* (2006.01)
*B04B 5/04* (2006.01)
(Continued)

(52) U.S. Cl.
CPC .......... *B01D 21/262* (2013.01); *B04B 5/0414* (2013.01); *B04B 5/0442* (2013.01);
(Continued)

(58) Field of Classification Search
CPC ........ B01D 21/262; B01D 21/26; C12N 1/00; C12N 5/0081; G01N 1/34; G01N 1/4077;
(Continued)

(56) References Cited

U.S. PATENT DOCUMENTS 4,255,256 A * 3/1981 Ferrante ................. B01D 43/00
210/730
5,407,579 A * 4/1995 Lee ....................... C07K 14/805
530/427

(Continued)

FOREIGN PATENT DOCUMENTS

CA 2358326 A1 4/2013
WO WO-2005030399 A1 * 4/2005 ............ B01L 3/5021

OTHER PUBLICATIONS

International Search Report and Written Opinion for International Patent Application No. PCT/US2018/040724, mailed Sep. 28, 2018 (8 pages).
(Continued)

*Primary Examiner* — Joseph W Drodge
(74) *Attorney, Agent, or Firm* — Nixon Peabody LLP

(57) ABSTRACT

A method is directed to separating contaminants from mammalian cells in an aqueous multiphase system, and includes loading a container with a liquid having a top liquid phase and a bottom liquid phase. A cover medium is inserted in the container with a mixture of cultured mammalian cells and contaminants. The container is incubated and centrifuged for respective periods of time. In response to the centrifuging, the cells are separated from the contaminants in accordance with the respective density of the cells, the contaminants, and each liquid phase, resulting in the cells being located at a liquid-to-liquid interface between the top liquid phase and the bottom liquid phase and the contaminants being located at the bottom of the container.

10 Claims, 27 Drawing Sheets

(51) Int. Cl.
- C12N 1/00 (2006.01)
- C12N 5/00 (2006.01)
- G01N 1/34 (2006.01)
- G01N 1/40 (2006.01)

(52) U.S. Cl.
CPC ............. *C12N 1/00* (2013.01); *C12N 5/0081* (2013.01); *G01N 1/34* (2013.01); *G01N 1/4077* (2013.01); *G01N 2001/4061* (2013.01); *G01N 2001/4083* (2013.01)

(58) Field of Classification Search
CPC ... G01N 2001/4061; G01N 2001/4083; G01N 1/40; B04B 5/00; B04B 5/04; B04B 5/0414; B04B 5/0442; B01L 3/50; B01L 3/5021
USPC ............................................ 210/789; 422/72
See application file for complete search history.

(56) References Cited

U.S. PATENT DOCUMENTS

| | | | | |
|---|---|---|---|---|
| 5,550,060 | A * | 8/1996 | Saunders | A61K 35/18 436/63 |
| 5,840,502 | A | 11/1998 | Van Vlasselaer | |
| 10,871,430 | B2 * | 12/2020 | Olechno | H01J 49/0031 |
| 2002/0058575 | A1 * | 5/2002 | Hlavinka | A61M 1/3693 494/3 |
| 2007/0259330 | A1 * | 11/2007 | Goddard | C12N 5/0605 435/372 |
| 2013/0045852 | A1 * | 2/2013 | Chapman | B01D 21/26 494/36 |
| 2013/0143727 | A1 * | 6/2013 | Emerson | B01L 3/50215 494/37 |
| 2015/0321203 | A1 * | 11/2015 | Chapman | G01N 33/491 494/37 |
| 2015/0343458 | A1 * | 12/2015 | Chapman | A61M 1/3693 422/548 |
| 2016/0124001 | A1 * | 5/2016 | Whitesides | G01N 33/80 435/2 |

OTHER PUBLICATIONS

Langdon, S. P.; *Methods in Molecular Medicine*; Langdon, S. P., Ed .; Humana Press Inc., 2004; vol. 88: Cancer, pp. 309-317 (11 pages).

Drexler, H. G.; Uphoff, C. C. *Cytotechnology*, 39, 75-90; 2002 (16 pages).

Olarerin-George, A. O., et al.; "Assessing the prevalence of mycoplasma contamination in cell culture via a survey of NCBI's RNA-seq archive"; *Nucleic Acids Res.*, vol. 43, No. 5, pp. 2535-2542; Feb. 24, 2015 (8 pages).

González-González, M. et al.; *Sep. Purif. Technol.* 158, pp. 103-107; 2016 (5 pages).

Clynes, M. M et al.; *In Vitro*; 16(9), pp. 809-812; Mar. 10, 1980 (4 pages).

Kuhlmann, I.; *Cytotechnology*; 19, 95-105; Jan. 12, 1996 (11 pages).

Cohen, S. et al.; *Tissue Eng.* vol. 12, No. 7, pp. 2025-2030; 2006 (7 pages).

Ryan, J.; "Understanding and Managing Cell Culture Contamination"; *Corning Tech. Bull.*; pp. 1-24; 2008 (24 pages).

Albertsson, P.-Å.; "Particle Fractionation in Liquid Two-Phase Systems"; *Biochim. Biophys. Acta*; vol. 27, pp. 378-395; 1958 (13 pages).

Mace, C. R. et al.; "Aqueous Multiphase Systems of Polymers and Surfactants Provide Self-Assembling Step-Gradients in Density"; *J. Am. Chem. Soc.* vol. 134, No. 22, pp. 9094-9097; Jun. 6, 2012 (10 pages).

Walter, H.; "Cell partitioning in two-polymer aqueous phase sytems"; *Trends Biochem. Sci.*; vol. 3, 97-100; May 1978 (4 pages).

Sousa, A. F., et al.; "A novel method for human hemotaopoietic stem/progenitor cell isolation from umbilical cord blood based on immunoaffinity aqueous two-phase partitioning"; *Biotechnol. Lett.* vol. 33, pp. 2373-2377; Aug. 21, 2011 (5 pages).

Fisher, D.; "The separation of cells an organelles by partitioning in two-polymer aqueous phases"; *Biochem. J.*, vol. 196, pp. 1-10; 1981 (10 pages).

Atefi, E et al.; "Interfacial Tension Effect on Cell Partition in Aqueous Two-Phase Systems"; *ACS Appl. Mater. Interfaces*, vol. 7, pp. 21305-21314; 2015 (10 pages).

Kumar, A. A.; Lim, C.; Moreno, Y.; Mace, C. R.; Syed, A.; Van Tyne, D.; Wirth, D. F.; Duraisingh, M. T.; Whitesides, G. M. *Am. J. Hematol.*, vol. 90, No. 1, pp. 31-36; Jan. 2015 (6 pages).

Kumar, A. A., et al.; "Density-based separation in multiphase systems provides a simple method to identify sickle cell disease"; *Proc. Natl. Acad. Sci. U. S. A.*, vol. 111, No. 41, pp. 14864-14869; Aug. 1, 2014 (6 pages).

Tavana, H. et al.; "Polymeric Aqueous Biphasic System Rehydration Facilitates High Throughput Cell Exclusion Patterning for Cell Migration Studies"; *Adv. Funct. Mater.* 21(15), 2920-2926; Aug. 9, 2011 (16 pages).

Frampton, J. P., et al.; "Aqueous two-phase system-mediated antibody micropatterning enables multiplexed immunostaining of cell monolayers"; *Biotechnol. J.*, vol. 10, pp. 121-125; Jul. 21, 2014 (7 pages).

Kubitschek, H. E., et al.; "Buoyant Density Constancy During the Cell Cycle of *Escherichia coli*"; *J. Bacteriol.* vol. 155, No., 3, pp. 1027-1032; Sep. 1983 (6 pages).

Bryan, A. K., et al.; "Measurement of mass, density, and volume during the cell cycle of yeast";*Proc. Natl. Acad. Sci. U. S. A.*, vol. 107, No. 3, pp. 999-1004; Jan. 19, 2010 (6 pages).

Wolff, D. A., et al.; "Separation of HeLa Cells by Colloidal Silica Density Gradient Centrifugation"; *J. Cell Biol.*, vol. 55, pp. 579-585; 1972 (7 pages).

Bryan, A. K., et al.; "Measuring single cell mass, volume, and density with dual suspended microchannel resonators"; *Lab Chip*, vol. 14, No. 3, pp. 569-576; Feb. 7, 2014 (16 pages).

Kruk, P. A., et al.; Letter to the Editor, "Percoll Centrifugation Eliminates Mold Contaminants from Cell Cultures"; *In Vitr. Cell. Dev. Biol.*, 27A, pp. 273-276; Apr. 1991 (6 pages).

Pertoft, H .; "Fractionation of cells and subcellular particles with Percoll"; *J. Biochem. Biophys. Methods*, vol. 44, pp. 1-30; 2000 (30 pages).

SooHoo, J. R., et al.; "Microfluidic aqueous two phase system for leukocyte concentration from whole blood"; *Biomed. Microdevices*, vol. 11, pp. 323-329; 2009 (7 pages).

Hatti-Kaul, R.; "Aqueous Two-Phase Systems"; *Mol. Biotechnol.*, vol. 19, pp. 269-277; 2001 (9 pages).

Kabeya, Y., et al.; "LC3, a mammalian homologue of yeast Apg8p, is localized in autophagosome membranes after processing"; *EMBO J.*, vol. 19, No. 21, pp. 5720-5728; 2000 (9 pages).

Orvedahl, A., et al.; "Auophagy Protects against Sindbis Virus Infection of the Central Nervous System"; *Cell Host Microbe*, vol. 7, pp. 115-127; Feb. 18, 2010 (13 pages).

Mizushima, N., et al.; "Methods in Mammalian Autophagy Research"; *Cell*, vol. 140, pp. 313-326; Feb. 5, 2010 (14 pages).

Lewis, C. L., et al.; "Mass and Density Measurements of Live and Dead Gram-Negative and Gram- Positive Bacterial Populations"; *Appl. Environ. Microbiol.*, vol. 80, No. 12, pp. 3622-3631; Jun. 2014 (10 pages).

Albertsson, P.-Å.; "Fractionation of Particles and Macromolecules in Aqueous Two-Phase Systems"; *Biochem. Pharmacol.*, vol. 5, pp. 351-358; 1961 (8 pages).

Pretlow, T. G., et al.; "Rate Zonal Centrifugation in a Ficoll Gradient"; *Anal. Biochem.*, vol. 29, pp. 230-237; 1969 (8 pages).

González-González, M., et al.; "Aqueous two-phase systems strategies to establish novel bioprocesses for stem cells recovery"; *Crit. Rev. Biotechnol.*, vol. 34, No. 4, pp. 318-327; 2014 (11 pages).

Ge, X., et al.; "Cell-Free Protein Expression under Macromolecular Crowding Conditions"; *PLoS ONE*, vol. 6, No. 12, e28707; doi:10.1371/journal.pone.0028707; 2011 (10 pages).

(56) References Cited

OTHER PUBLICATIONS

Croll, T., et al.; "Analysis of the Phase Behavior of the Aqueous Poly(ethylene glycol)-Ficoll System"; *Biotechnol. Prog.*, vol. 19, No. 4, pp. 1269-1273; May 6, 2003 (5 pages).

Freshney, R. I.; *Culture of Animal Cells*, 6th ed.; John Wiley & Sons, Inc.: Hoboken, NJ, 2010 (676 pages).

Fischer, D., et al.; "In vitro cytotoxicity testing of polycations: influence of polymer structure on cell viability and hemolysis"; *Biomaterials*, vol. 24, pp. 1121-1131; 2003 (11 pages).

OptiPrep TM The ideal density gradient medium for isolation of macromolecules and lipoproteins http://www.axis-shield-density-gradient-media.com/Purification and analysis of viruses.pdf. (Accessed May 30, 2017) (4 pages).

* cited by examiner

|  | Density (g/mL) | Osmolality (mmol/kg) | pH |
|---|---|---|---|
| Top Phase | 1.0428 ± 0.0002 | 299 ± 1 | 7.5 ± 0.1 |
| Bottom Phase | 1.0747 ± 0.0006 | 306 ± 6 | 7.3 ± 0.1 |

FIG. 2

|  | Percent Recovery | Control Viability | Recovered Viability |
|---|---|---|---|
| Trial 1 | 74.5 ± 3.3 | 95.7 | 97.3 ± 0.1 |
| Trial 2 | 74.0 ± 3.8 | 96.1 | 96.1 ± 0.7 |
| Trial 3 | 75.5 ± 2.3 | 93.9 | 95.0 ± 0.5 |
| Trial 4 | 71.8 ± 2.5 | 96.7 | 97.2 ± 0.8 |
| Trial 5 | 76.3 ± 6.3 | 96.4 | 97.8 ± 0.4 |
| Average | 74.4 ± 1.5 | 95.7 ± 0.5 | 96.7 ± 0.3 |

FIG. 3

| CFU Counts | | | |
|---|---|---|---|
| | Trial 1 | Trial 2 | Trial 3 |
| Contaminated | 9700 | 39000 | 28000 |
| ATPS Treated | 3800 | 7700 | 31000 |
| % Difference | 60.8 | 80.3 | -10.7 |

| Flow Cytometry: Cell-Bacteria Aggregates (% of Events) | | | |
|---|---|---|---|
| | Trial 1 | Trial 2 | Trial 3 |
| Contaminated | 0.9 | 4.0 | 21.8 |
| ATPS Treated | 0.4 | 2.5 | 20.7 |
| % Difference | 55.6 | 37.5 | 5.0 |

| Flow Cytometry: Total Bacteria (% of Events) | | | |
|---|---|---|---|
| | Trial 1 | Trial 2 | Trial 3 |
| Contaminated | 1.7 | 4.7 | 15.6 |
| ATPS Treated | 1.0 | 3.2 | 14.3 |
| % Difference | 42.0 | 31.2 | 8.4 |

FIG. 7

| | Initial | Recovered | Day 3 |
|---|---|---|---|
| Control | 25000 | -- | 6000 |
| ATPS | 31000 | 5100 | 1600 |

FIG. 8

| 0.6X PBS | Density (g/mL) | Osmolality (mmol/kg) |
| --- | --- | --- |
| Top | 1.0423 | 296 |
| Bottom | 1.0754 | 291 |

| 0.65X PBS | Density (g/mL) | Osmolality (mmol/kg) |
| --- | --- | --- |
| Top | 1.0424 | 302 |
| Bottom | 1.0761 | 302 |

| 0.7X PBS | Density (g/mL) | Osmolality (mmol/kg) |
| --- | --- | --- |
| Top | 1.0428 | 321 |
| Bottom | 1.0763 | 320 |

FIG. 9

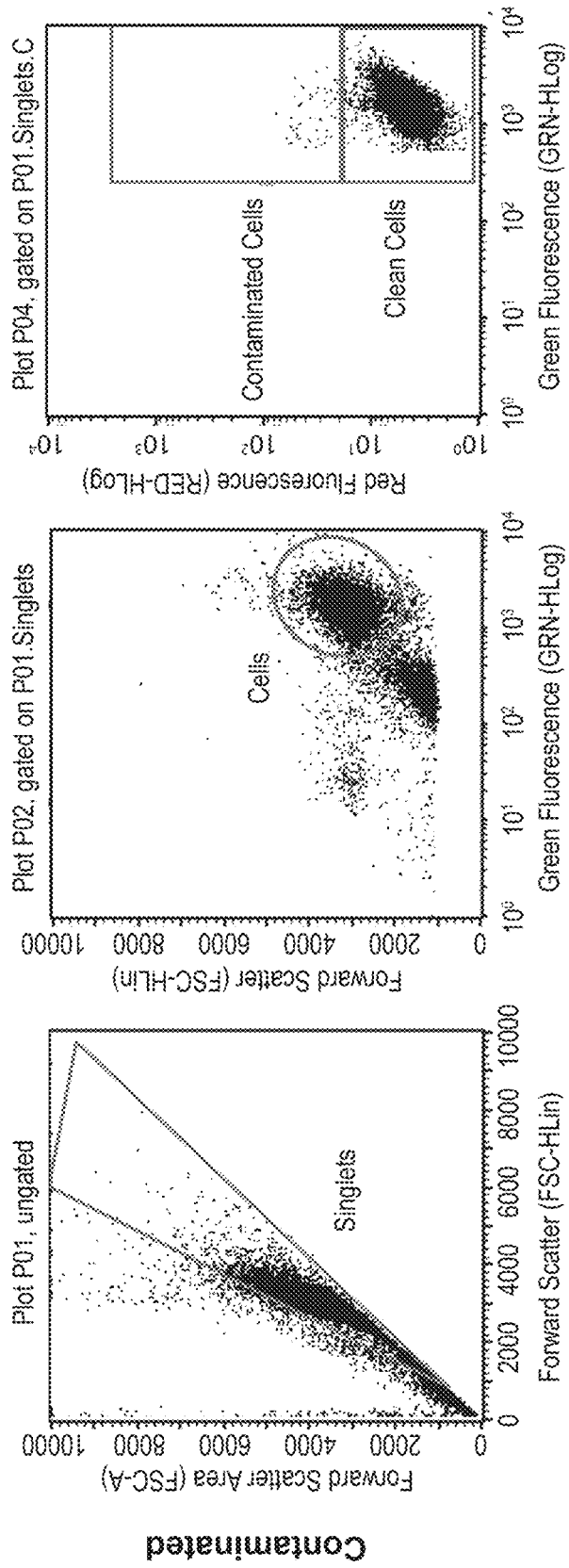

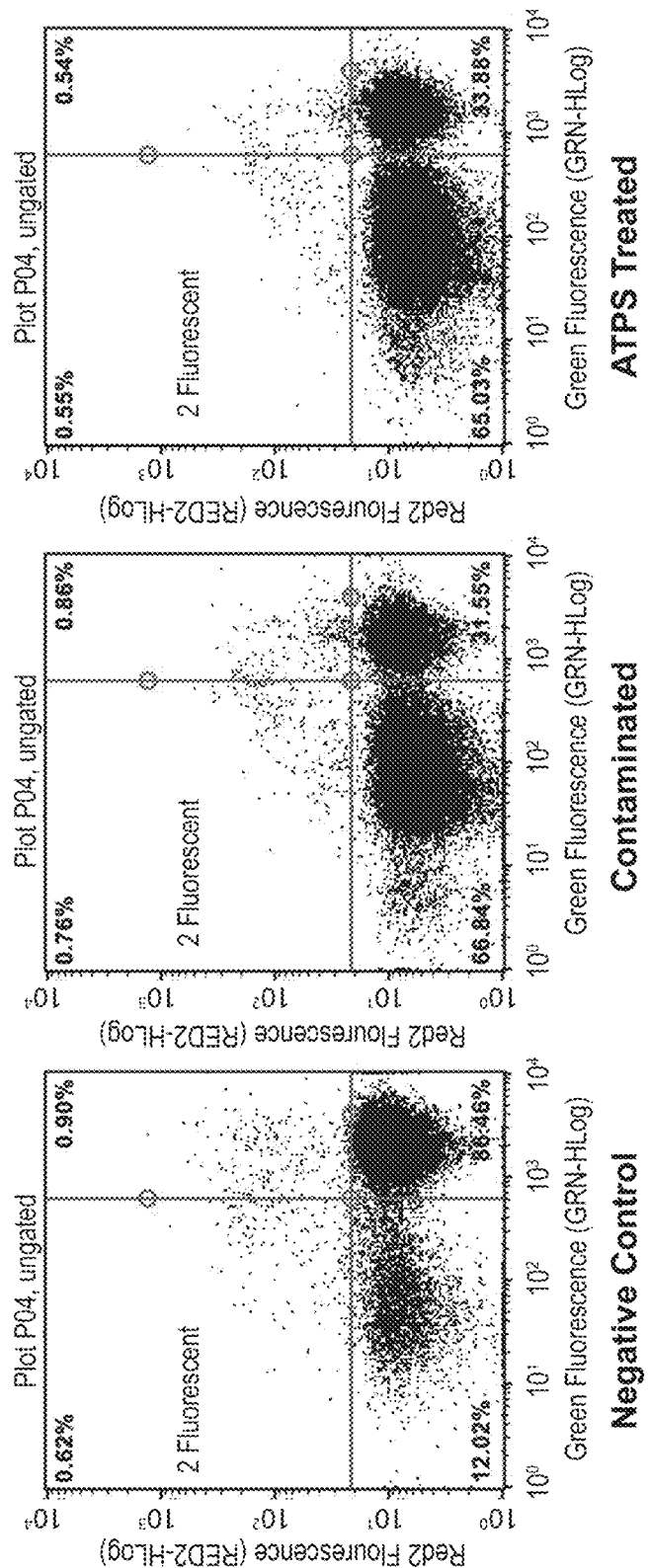
FIG. 11A Negative Control
FIG. 11B Contaminated
FIG. 11C ATPS Treated

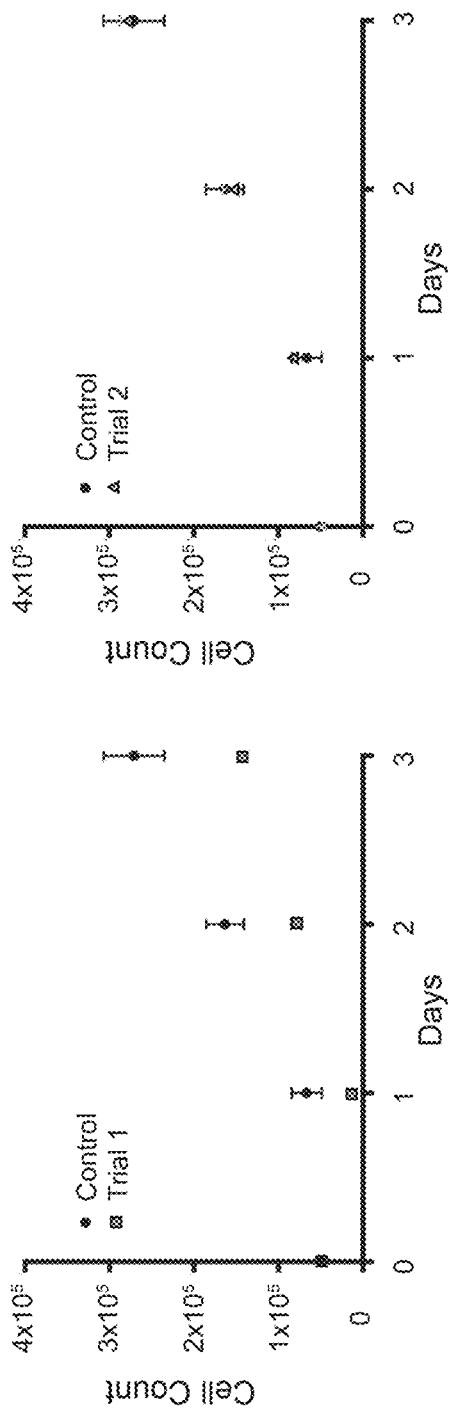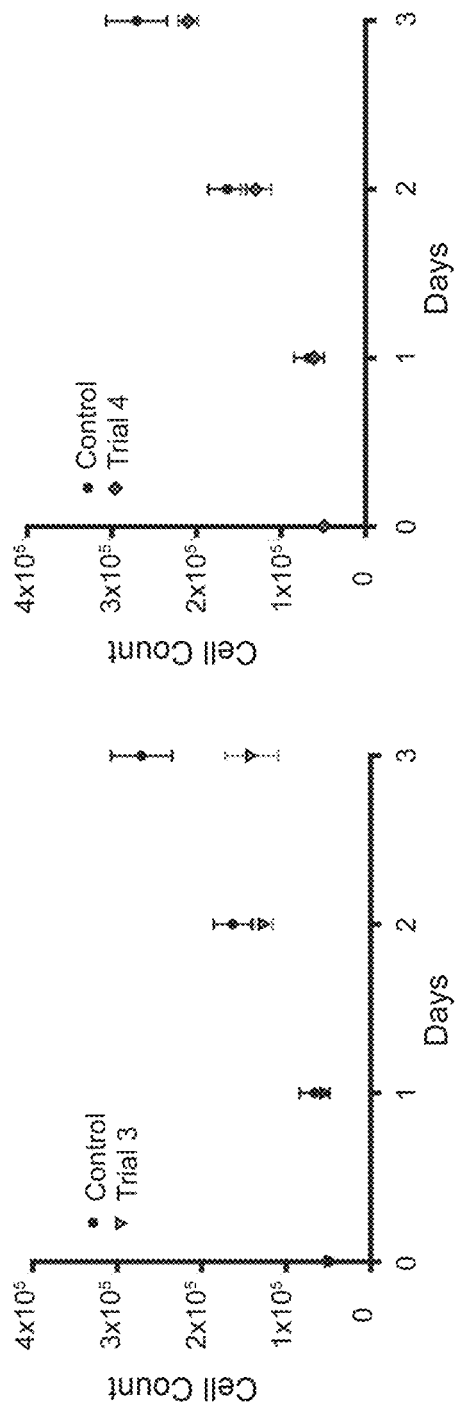
FIG. 13A  FIG. 13B  FIG. 13C  FIG. 13D

Density, Osmolality, and pH of the Top and Bottom Phases of Our ATPS[α]

| top phase | | | |
|---|---|---|---|
| stock | density (g/mL) | osmolality (mOsm/kg) | pH |
| 1 | 1.0431 | 296 | 7.37 |
| 2 | 1.0432 | 289 | 7.36 |
| 3 | 1.0434 | 292 | 7.37 |
| 4 | 1.0435 | 289 | 7.39 |
| 5 | 1.0434 | 294 | 7.40 |
| average | 1.0433 | 292 | 7.38 |
| stdev | 0.0002 | 3 | 0.02 |
| SEM | 0.0001 | 1 | 0.01 |

| bottom phase | | | |
|---|---|---|---|
| stock | density (g/mL) | osmolality (mOsm/kg) | pH |
| 1 | 1.0762 | 296 | 7.42 |
| 2 | 1.0755 | 289 | 7.35 |
| 3 | 1.0755 | 292 | 7.35 |
| 4 | 1.0751 | 296 | 7.41 |
| 5 | 1.0752 | 299 | 7.37 |
| average | 1.0755 | 294 | 7.38 |
| stdev | 0.0004 | 4 | 0.03 |
| SEM | 0.0002 | 2 | 0.01 |

[α]Uncertainty reported is standard deviation and error of the mean (N = 5 replicates).

FIG. 15

Focused study on the reproducibility of density, osmolality, and pH of ATPS prepared from 7% (w/w) PEG and 11% (w/w) Ficoll. These values can be compared to the values obtained from generating the ATPS from a different stock solution each time (Table 1)

Top Phase

| Replicate | Density (G/mL) | Osmolality (mOsm/kg) | pH |
|---|---|---|---|
| 1 | 1.0431 | 296 | 7.37 |
| 2 | 1.0430 | 301 | 7.38 |
| 3 | 1.0431 | 301 | 7.37 |
| 4 | 1.0431 | 296 | 7.38 |
| 5 | 1.0432 | 297 | 7.40 |
| 6 | 1.0432 | 305 | 7.40 |
| 7 | 1.0431 | 299 | 7.40 |
| 8 | 1.0431 | 300 | 7.39 |
| 9 | 1.0430 | 297 | 7.41 |
| 10 | 1.0431 | 298 | 7.41 |
| Average | 1.0431 | 299 | 7.39 |
| Stdev | 0.0001 | 3 | 0.02 |
| SEM | 0.0000 | 1 | 0.00 |
| %CV | 0.01 | 0.9 | 0.21 |

Bottom Phase

| Replicate | Density (G/mL) | Osmolality (mOsm/kg) | pH |
|---|---|---|---|
| 1 | 1.0762 | 296 | 7.42 |
| 2 | 1.0762 | 305 | 7.37 |
| 3 | 1.0762 | 304 | 7.42 |
| 4 | 1.0762 | 302 | 7.43 |
| 5 | 1.0762 | 304 | 7.39 |
| 6 | 1.0761 | 305 | 7.39 |
| 7 | 1.0762 | 300 | 7.39 |
| 8 | 1.0762 | 297 | 7.41 |
| 9 | 1.0763 | 298 | 7.41 |
| 10 | 1.0761 | 305 | 7.37 |
| Average | 1.0762 | 302 | 7.40 |
| Stdev | 0.0001 | 4 | 0.02 |
| SEM | 0.0000 | 1 | 0.01 |
| %CV | 0.01 | 1.2 | 0.29 |

FIG. 16

Percent of Cells Added to the ATPS Recovered from the
Interface with Their Respective Viabilities[α]

| | HL-60 II | | |
|---|---|---|---|
| | percent recovery | control recovery | recovered viability |
| Trial 1 | 57.2 ± 7.1 | 99.8 | 99.4 ± 0.1 |
| Trial 2 | 53.4 ± 2.5 | 98.1 | 89.4 ± 8.7 |
| Trial 3 | 61.1 ± 3.6 | 96.3 | 97.5 ± 0.3 |
| Trial 4 | 51.7 ± 3.1 | 94.5 | 95.0 ± 0.1 |
| average | 55.9 ± 2.1 | 97.2 ± 1.1 | 95.3 ± 2.2 |

[α]Each trial represents a biological replicate, which is the average of 3 technical replicates. A single control was analyzed for each trial. Final averages are of all replicates ($N = 12$ for ATPS, $N = 4$ for controls). Uncertainty shown is standard error of the mean.

FIG. 17

AQUEOUS TWO-PHASE SYSTEM FOR THE SEPARATION AND RECOVERY OF MAMMALIAN CELLS FROM CONTAMINATED CULTURES

CROSS-REFERENCE TO RELATED APPLICATIONS

This application is a national stage of International Application No. PCT/US2018/040724, filed on Jul. 3, 2018, which claims priority to U.S. Provisional Patent Application Ser. No. 62/528,209, filed Jul. 3, 2017, each of which is hereby incorporated by reference herein in its entirety.

FIELD OF THE INVENTION

The present invention relates generally to an aqueous multiphase system, and, more particularly, to separating cultured mammalian cells from contaminants.

BACKGROUND OF THE INVENTION

The in vitro culture of mammalian cells is a crucial part of biomedical research. Aseptic technique is necessary to ensure that only the cells of interest are growing in the culture. Contamination, however, is still a relatively common occurrence in cell culture laboratories. Typical contaminants include bacteria, yeast, and mold. These microorganisms affect the way cells behave in culture (e.g., change morphology, growth, and viability) and alter the culture conditions (e.g., by changing pH or by competing for resources in the medium). Nonviable cells (i.e., cells present in culture that lack membrane integrity as demonstrated by the inability to exclude dyes), cell fragments, and debris can also be considered contaminants because their presence can bias seeding densities or skew the results of functional assays. Cultures that contain a large fraction of nonviable cells (e.g., cultures that are overgrown) may not be usable unless the viable cells can be isolated from the dead cells.

Antibiotics, such as penicillin and streptomycin, are used to treat contamination or prevent it prophylactically. However, these compounds may adversely interfere with normal processes in cultured cells, exacerbate contamination issues by masking poor aseptic technique, or promote antibiotic resistance and the development of resistant microorganisms. Ideally, the use of antibiotics in cell culture should be eliminated or minimized. To prevent the spread of microorganisms to other cultures and to avoid the negative effects of antibiotic use, contaminated cultures are typically destroyed with bleach. Although this approach is an effective way to contain and eliminate contaminants, it also results in the disposal of the cultured cells. This is, at a minimum, a waste of time and effort for the researchers and money for the lab. Moreover, if the cells are rare or valuable (e.g., primary or engineered), their disposal may not be acceptable. The capability to decontaminate and recover the desired population of cells would be far more appropriate in these cases.

The present disclosure is directed to method and system for separating contaminants from mammalian cells in an aqueous multiphase system that solves the above and other needs.

SUMMARY OF THE INVENTION

According to one aspect of the present invention, a method is directed to separating contaminants from mammalian cells in an aqueous multiphase system. The method includes loading a container with a liquid having a top liquid phase and a bottom liquid phase, the top liquid phase being separated from the bottom liquid phase at a liquid-to-liquid interface. The top liquid phase has a top liquid density that is different than a bottom liquid density of the bottom liquid phase, and the container has a top open end and a bottom closed end. A cover medium is inserted in the container, the cover medium including a mixture of cultured mammalian cells and contaminants, and the mixture remaining initially in a mixed form during a first time period.

The cultured mammalian cells have a cell density and the contaminants have a contaminant density, the cell density being different than the contaminant density. The container, containing the liquid and the cover medium, is, then, centrifuged for a second time period subsequent to the first time period. In response to the centrifuging and in accordance with the respective density, the cultured mammalian cells are separated from the contaminants, the cultured mammalian cells being located at the liquid-to-liquid interface between the top liquid phase and the bottom liquid phase, and the contaminants being located at the bottom closed end of the container.

According to another aspect of the present invention, an aqueous multiphase system is directed to separating contaminants from mammalian cells. The system includes a container having a top open end and a bottom closed end, and a liquid located within the container. The liquid includes a top liquid phase with a top liquid density and a bottom liquid phase with a bottom liquid density, the top liquid phase being separated from the bottom liquid phase at a liquid-to-liquid interface. The top liquid density is different than the bottom liquid density.

The system further includes a cover medium with a mixture of cultured mammalian cells and contaminants, the mixture remaining initially in a mixed form during a first time period prior to being inserted into a centrifuge. The cultured mammalian cells have a cell density and the contaminants have a contaminant density, the cell density being different than the contaminant density. In response to the container being inserted into the centrifuge for a second time period, which is subsequent to the first time period, and based on their respective density, the cultured mammalian cells are subsequently located at the liquid-to-liquid interface and the contaminants are located at the bottom closed end.

According to yet another aspect of the present invention, a method is directed to separating contaminants from mammalian cells in an aqueous multiphase system, and includes loading a liquid in a tube. In response to adding a mixture selected from a group consisting of at least one polymer and at least one salt, forming a multiphase liquid having a first phase and a second phase. Each phase of the multiphase liquid has a respective and distinct phase density including a first density of the first phase and a second density of the second phase. A culture of mammalian cells mixed with contaminants is added in the multiphase liquid, the mammalian cells having a cell density that is greater than the first density but less than the second density, and the contaminants having a contaminant density that is greater than the cell density and the second density.

The tube contains, containing the multiphase liquid with the culture of mammalian cells mixed with contaminants, is inserted into a centrifuge in which the tube is centrifuged. In response to the centrifuging, the mammalian cells are accumulated between the first phase and the second phase and the contaminants are sedimented at a bottom of the tube.

Additional aspects of the invention will be apparent to those of ordinary skill in the art in view of the detailed description of various embodiments, which is made with reference to the drawings, a brief description of which is provided below.

BRIEF DESCRIPTION OF THE DRAWINGS

FIG. 2 is a table showing test results of an aqueous two-phase system ("ATPS").

FIG. 3 is a table showing a percentage of cells added to the ATPS that are recovered from the interface.

FIG. 7 is a table showing quantitative measurements of a separation efficiency of the PEG-Ficoll ATPS.

FIG. 8 is a table that shows CFU/ml counts for contaminated cell suspensions.

FIG. 9 is a table that shows results from a 7% (w/w) PEG—11% (w/w) Ficoll ATPS.

FIG. 10D shows a representative image of flow cytometry data for contaminated positive control of singlets.

FIG. 10E shows a representative image of flow cytometry data for contaminated positive control of cells.

FIG. 10F shows a representative image of flow cytometry data for contaminated positive control of contaminated and clean cells.

FIG. 11A shows a representative image of negative control for ungated scatter plots of a trial.

FIG. 11B shows a representative image of contaminated positive control for ungated scatter plots of a trial.

FIG. 11C shows a representative image of ATPS-treated samples for ungated scatter plots of a trial.

FIG. 13A shows a growth curve for a first trial of individual biological replicates of HeLa cells recovered from the interface of a PEG-Ficoll ATPS.

FIG. 13B shows a growth curve for a second trial of individual biological replicates of HeLa cells recovered from the interface of a PEG-Ficoll ATPS.

FIG. 13C shows a growth curve for a third trial of individual biological replicates of HeLa cells recovered from the interface of a PEG-Ficoll ATPS.

FIG. 13D shows a growth curve for a fourth trial of individual biological replicates of HeLa cells recovered from the interface of a PEG-Ficoll ATPS.

FIG. 15 is a table showing density, osmolality, and pH of top and bottom phases of ATPS.

FIG. 16 is a table showing a focused study on the reproducibility of density, osmolality, and PH of ATPS prepared from 7% (w/w) PEG and 11% (w/w) Ficoll.

FIG. 17 is a table showing percent of cells added to ATPS recovered from an interface with their respective viabilities.

Figure 1A:
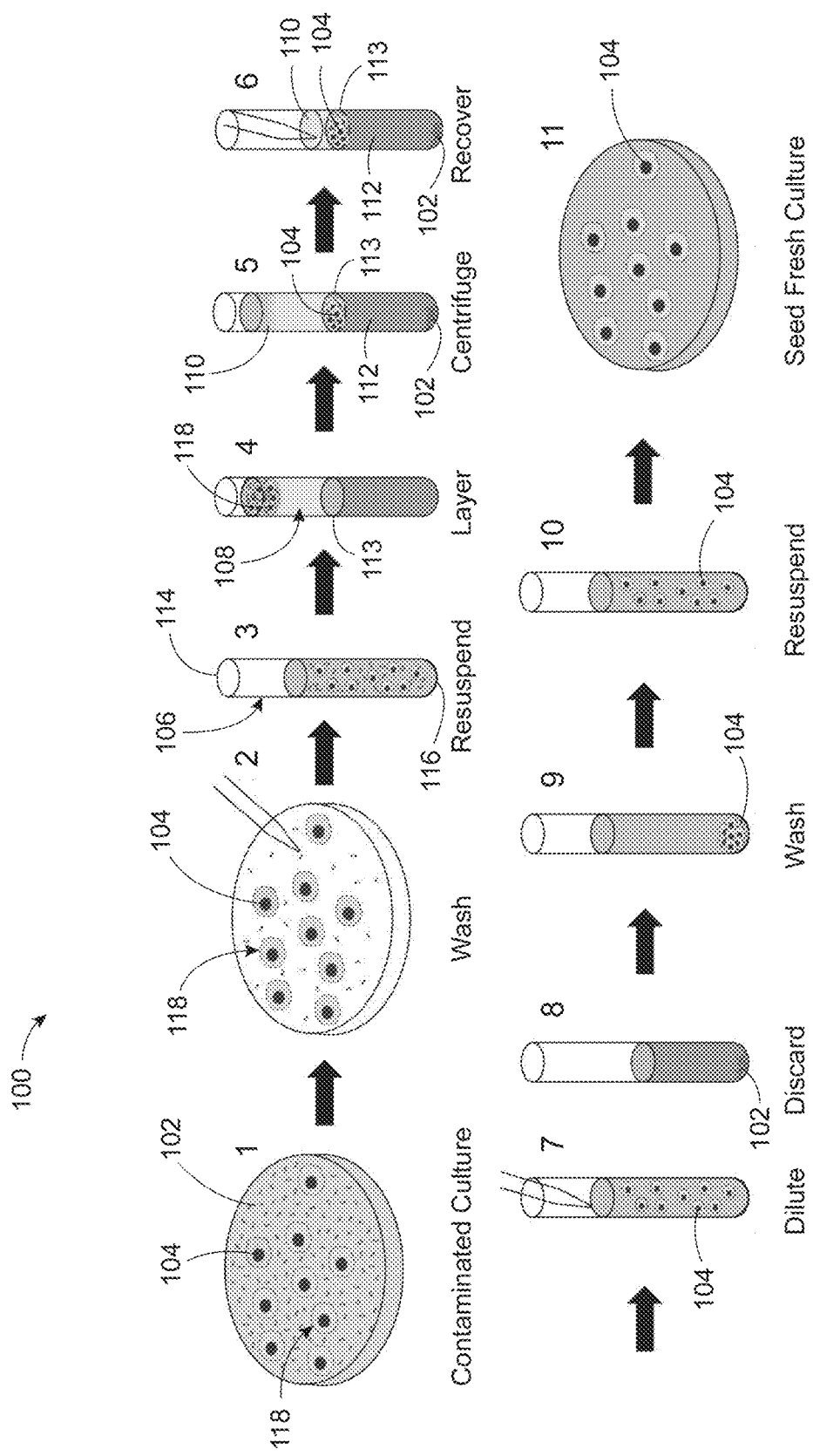
FIG. 1A is a schematic representation of a cell culture decontamination procedure using an aqueous multiphase system.

While the invention is susceptible to various modifications and alternative forms, specific embodiments have been shown by way of example in the drawings and will be described in detail herein. It should be understood, however, that the invention is not intended to be limited to the particular forms disclosed. Rather, the invention is to cover all modifications, equivalents, and alternatives falling within the spirit and scope of the invention as defined by the appended claims.

DETAILED DESCRIPTION

While this invention is susceptible of embodiment in many different forms, there is shown in the drawings and will herein be described in detail preferred embodiments of the invention with the understanding that the present disclosure is to be considered as an exemplification of the principles of the invention and is not intended to limit the broad aspect of the invention to the embodiments illustrated. For purposes of the present detailed description, the singular includes the plural and vice versa (unless specifically disclaimed); the words "and" and "or" shall be both conjunctive and disjunctive; the word "all" means "any and all"; the word "any" means "any and all"; and the word "including" means "including without limitation." Where a range of values is disclosed, the respective embodiments include each value between the upper and lower limits of the range.

Generally, embodiments described below refer to a density-based method for removing contaminants, including microorganisms and nonviable cells, from mammalian cell cultures using an ATPS. The physical properties of a polyethylene glycol ("PEG")—Ficoll ATPS can be tuned to prepare a biocompatible system that removes contaminants without adversely affecting the viability or growth of the cultured cells after treatment. This system is used to enrich cell culture populations for viable cells and to reduce the number of microorganism contaminants in a culture, which increases the chances of subsequent antibiotic treatments being successful. By removing unwanted cells, desired cell populations are recovered and cultures that would otherwise need to be disposed of can continue to be used.

For example, a method is directed to separating cultured mammalian cells from contaminants based on density using ATPS. This method allows recovered cells to be cultured after decontamination and eliminates or minimizes the need for antibiotic treatments. ATPS form when solutions of certain water-soluble polymers are mixed above a threshold concentration and molecular weight. These systems form two thermodynamically stable phases with different physical properties (e.g., densities) separated by a liquid-liquid interface. More generally, aqueous systems composed of multiple phases are known as aqueous multiphase systems ("AMPS"). Because water is the common solvent, ATPS are particularly well suited for separations of biomolecules and cells when compared to immiscible systems prepared using organic solvents. Cells are partitioned into either phase due to properties of cell surfaces or the interfacial tension of the system. Cells are also isolated based on density at the liquid-liquid and liquid-container interfaces. Other applications that capitalize on the biocompatibility of ATPS include patterning cells or biomolecules to perform functional assays.

Microorganisms that may contaminate cell cultures such as bacteria (e.g., *E. coli*) and yeast have higher buoyant densities than cultured mammalian epithelial cells (e.g., HeLa, human lung epithelial, and mouse lymphocytic leukemia). Under these conditions, contaminated cultures added to an ATPS will separate by density upon centrifugation with the mammalian cells sedimenting to the liquid-liquid interface and the denser contaminates forming a pellet at the bottom of the container. After separation, the desired cells are recovered from the interface by pipette, washed, and transferred to fresh medium for further culture (see FIG. 1A). An ATPS is prepared from PEG and Ficoll (polysucrose) whose phases form a step in density that is able to separate lower density mammalian cells from higher density microorganisms in a test system of HeLa cells and *E. coli*. This system of biocompatible polymers allows for the cells to be separated and recovered without a loss of viability. Furthermore, recovered cells have comparable viability and growth rates to control populations that are not introduced to ATPS.

By exploiting an intrinsic physical difference between mammalian cells and contaminant microorganisms, the desired cell population is enriched for, thereby minimizing the need for treatments with antimicrobial compounds. Separating cells from contaminants in ATPS based on density is a simple, gentle, and nondestructive process. Using ATPS is preferable to continuous density gradients (e.g., Percoll):

(i) the sharp step in density between phases in ATPS allow cells with slightly different densities to become concentrated at an interface rather than in a disperse band; and (ii) the interface allows for desired cells and contaminants to be separated from each other by significant phase volume, with this separation in space making it easier to remove cells by pipette without also recovering the contaminants.

Density-based separation of cell populations allows non-viable and lysed cells to be similarly separated and removed, enriching the cell population for viable cells with similar densities. Separation of nonviable cells and cell debris from viable cells by partitioning to separate phases of an ATPS is achieved in a more controllable manner by characterizing and tuning the physical properties of the phases and by considering the interface as a region of the system distinct from the bulk phases. The disclosed ATPS-based cell recovery method allows for the preservation of potentially valuable cells that would otherwise be discarded.

Experimental Section

Model System for Contaminated Cultures

To confirm separation and determine the efficiency of the disclosed method, model contaminated cultures were developed using GFP-expressing HeLa cells and mPlum-expressing *E. coli*. These fluorophores were chosen to avoid overlap in emission, which allowed differentiation between the two types of cells by fluorescence. The model contaminated cultures were created by adding fluorescent microorganisms to cell cultures. After treating these cultures with ATPS, the cultures were qualitatively inspected for the presence of red *E. coli* using confocal microscopy. For a quantitative measure of separation efficiency and number of bacteria present after separation, flow cytometry and colony formation assays were used. Through confocal microscopy, the morphology of the HeLa cells was observed to ensure that it was unchanged by the separation process. These images also provided information regarding the interaction of the microorganisms with the cells.

Design of Aqueous Two-Phase Systems

The inherent difference in density between mammalian cells and microorganisms allows them to be separated by centrifugation when placed in a density gradient or ATPS. ATPS provide a sharp step in density at the liquid-liquid interface, which can be used to isolate cells of interest. HeLa cells have a buoyant density of 1.04-1.07 g/mL, while yeast and *E. coli* have reported buoyant densities of 1.08-1.11 g/mL and 1.12-1.18 g/mL, respectively. Based on these values, an ATPS is desired with a bottom phase that is denser than mammalian cells but less dense than microorganisms. This means that, upon centrifugation, the microorganisms can sediment through the entire system and form a pellet at the bottom of the container. The desired mammalian cells, however, localize to the liquid-liquid interface allowing them to be subsequently recovered and cultured.

PEG-Ficoll is among the more than 100 known combinations of polymers that form ATPS. One benefit of these polymers is that they are biocompatible. The densities, osmolalities, and pH of the phases, as well as the interfacial tension between phases can be tuned through control of polymer and buffer concentrations to provide the desired separation while maintaining biocompatibility.

An ATPS was developed with a top phase density of 1.0428±0.0002 g/mL and a bottom phase density of 1.0747±0.0006 g/mL, which would allow for the desired separation of HeLa and *E. coli* cells. Based on an evaluation of several relative concentrations of PEG and Ficoll, final concentrations of 7% w/w PEG (8,000 g/mol) and 11% w/w Ficoll (400,000 g/mol) were selected because they produced the desired densities for the cell separation systems. PEG 8K was chosen because it allows for sterilization by filtration using 0.22 μm filters, while larger molecular weight PEG does not. To ensure biocompatibility, a range of phosphate buffered saline (PBS) concentrations was tested (see FIG. 9), finding that systems prepared in 0.65× PBS yielded a top phase osmolality of 299±1 mmol/kg, pH 7.5±0.1, and a bottom phase osmolality of 306±6 mmol/kg, pH 7.3±0.1 (see FIG. 2). This ATPS formulation allows the cells to be separated without adversely affecting their morphology and viability.

Materials and Methods

Preparation of Aqueous Two-Phase Systems

Stock solutions of 14% w/w PEG (Amresco, average molecular weight 8,000 g/mol) and 22% w/w Ficoll (Corning, average molecular weight 400,000 g/mol) were prepared in 0.65× PBS, diluted from 10× stock (Fisher Scientific). These solutions were sterilized by vacuum filtration through "Steriflip" 0.22 μm filters (EMD Millipore). Three grams of each stock solution were added to a 15-mL conical tube for a final overall concentration of 7% w/w PEG and 11% w/w Ficoll. The systems were vortexed for ~20 seconds to ensure complete mixing then centrifuged at 1500 g for 15 minutes to achieve phase separation. The phases were divided by pipetting the top phase and draining the bottom phase through a hole pierced in the bottom of the conical tube in order to avoid remixing. The physical properties of each phase (i.e., density, osmolality, and pH) were characterized. The densities were measured using an Anton Paar DMA 4100M density meter, the osmolalities were measured using a Wescor Vapro Model 5600 vapor pressure osmometer, and pH was measured using a VWR Symphony B10P pH meter.

Culture of Cells and Microorganisms

GFP-expressing HeLa cells were cultured in Dulbecco's Modified Eagle Medium (DMEM; Corning) with 10% fetal bovine serum (FBS; Gibco) at 37° C., and 5% $CO_2$. mPlum-expressing *E. coli*, which are ampicillin resistant and having the mPlum expression under a pBad promoter, were grown in Lysogeny Broth (LB; Amresco) to an $OD_{600}$ of 0.6-0.7, and, then, induced with 0.2% w/v L-arabinose (Acros Organics) and allowed to grow 15 hours. After induction, red fluorescence was confirmed by fluorescence microscopy.

Separation of Cell Contaminants

The medium in the contaminated HeLa cell culture was removed by pipette and the adherent cells were washed with 1× PBS. The cells were then trypsinized (0.25%+EDTA; HyClone, GE Life Sciences) for 5 minutes at 37° C. to facilitate removal from a 60-mm plate. Next, the cells were pelleted by centrifugation (200 g for 5 minutes) and resuspended in 1 mL of complete culture medium. This suspension was layered on top of the ATPS by pipette. The system was centrifuged for 15 minutes at 2000 g to allow the contaminants to sediment to the bottom of the tube and the mammalian cells to sediment to the liquid-liquid interface. The top phase was aspirated by pipette leaving approximately 0.5 mL above the interface. The liquid close to and including the interface (~2 mL) was transferred by pipette into a 15-mL conical tube containing 3 mL of fresh Leibovitz Medium (L-15; HyClone, GE Life Sciences) to dilute the polymer solutions and prevent further phase-separation. L-15 was used for this step because the pH of DMEM is above physiological pH in atmospheric $CO_2$ concentrations. This solution was centrifuged for 10 minutes at 200 g to pellet the recovered cells. The cells were then washed twice with 1 mL L-15. Finally, they were diluted to the desired density to seed new plates or for analysis (see FIG. 1A).

Viability Enrichment

To determine the ability to enrich cell populations for viable cells, $1\times10^6$ cells were seeded in a 60-mm plate and left in the incubator for seven days without exchanging media, which led to severe overgrowth. The DMEM was removed along with cells in suspension and reserved for analysis while the adherent cells were trypsinized to remove them from the plate. These cells were passed through the PEG-Ficoll ATPS and the cells from the interface were recovered. Viability was analyzed using propidium iodide exclusion and quantified with flow cytometry (EMD-Millipore Guava easyCyte Flow Cytometer 6HT-2L).

Imaging and Analysis of Model Contaminated Systems

To measure the efficiency of our separation method, GFP-HeLa cultures were grown to confluency. The DMEM was removed from the cultures and replaced with 3 mL of L-15 to allow for incubation in atmospheric $CO_2$. 1 mL of a suspension of mPlum E. coli ($OD_{600} \approx 1.0$) was added to the cultures and allowed to incubate for 30 minutes. These cultures were then treated using the ATPS method described above. The cultures were analyzed for the presence of contaminants before and after treatment by microscopy, flow cytometry, and colony formation assays. Contaminated and recovered cells were imaged by confocal microscopy (Leica DMi8 with Andor Revolution DSD2 confocal imaging system). HeLa cells were imaged using a GFP filter and E. coli using an RFP filter with a 20× lens (NA=0.4, WD=0-2 mm). Cultures were analyzed for the presence of GFP- and mPlum-expressing cells. Cell counts for percent recovery calculations were performed using a Coulter Counter z2 (Beckman Coulter) or a Countess II Automated Cell Counter (ThermoFisher).

Flow Cytometry

Cells were analyzed using two different methods. The first method was designed to identify GFP-HeLa cells that had mPlum E. coli bound to them both before and after separation. This population was identified by first gating for single cells, then for cells that were positive for green fluorescence, and then for cells that were positive for red fluorescence (see FIGS. 10A-10I). The second method was designed to identify all red-fluorescing species in the suspension, which would include free E. coli but would differentiate it from debris. These cells were identified by simply gating for all events that were positive for red fluorescence (see FIGS. 1A-11C).

Colony Formation Assay

Contaminated cell suspensions were serially diluted by a factor of 10 with PBS. 10 µL of undiluted, 1:10, 1:100, and 1:1000 suspensions were added to the top of an agar plate in a line. The plate was tilted to allow the droplets to run vertically down the plate until they reached the bottom. These plates were incubated at 37° C. for ~15 hours and imaged with a digital camera. Single colonies were identified by eye and counted using ImageJ to record the analysis (FIGS. 12A-12D).

Treatment Effectiveness

To determine if the ATPS treatment sufficiently reduced the bacteria count low enough to prevent recurrence of contamination, the recovered HeLa cells were cultured in DMEM containing antibiotic for one passage cycle and compared to cells cultured without antibiotic and without ATPS treatment. Colony formation assays were performed prior to treatment with ATPS method and again after 3 days in culture.

Statistical Analysis

Prism 7 (GraphPad) was used for all statistical analyses including generating plots, fitting curves to data, performing student's t-tests, and comparing linear regression slope comparison.

Results and Discussion

Recovery of Mammalian Cells

The recovery percentage is important for continuing a cell culture after decontamination treatment because higher cell counts are often required for seeding or other downstream applications. Significant loss of desired cells during separation could inhibit the culture's ability to grow after recovery particularly for slow growing or fragile cells. The density-based method developed relies on the fact that most of the desired cells will sediment to the liquid-liquid interface where they can easily be recovered. The biocompatibility of the process is also essential because if the recovered cells are damaged or too few cells are recovered, it will not be possible to start a new culture from them. The majority of the desired cells can be isolated according to their density and recovered without substantial loss of cells. An average of 74.4±1.5% of the HeLa cells were recovered and added to the ATPS after removing them from the interface by pipette and washing them (see FIG. 3). Loss of cells was likely due to some fraction of the cell population having a different density from the recovered cells as well as adsorption of cells to the pipette tips and conical tubes during separation and wash steps.

Maximizing viability throughout the separation procedure is essential for maintaining these cells in culture after the contaminants are removed. Recovered cells had an average viability of 96.7±0.3% compared to control with a viability of 95.7±0.5% (see FIG. 3). The control population was aliquoted from the same suspension of cells but was not passed through an ATPS. This data indicates that subjecting the cells to this decontamination procedure, which includes exposure to polymer solutions, relatively high-speed centrifugation, and several pipetting steps, does not result in a loss of viability relative to control. The average viability of cells passed through our ATPS was not significantly different from cells passaged using standard cell culture technique (p value=0.2). Because calculations of seeding densities often rely on cell counts, maximizing viability while eliminating nonviable cells allows for more accurate seeding of subsequent cultures.

Figure 4A:
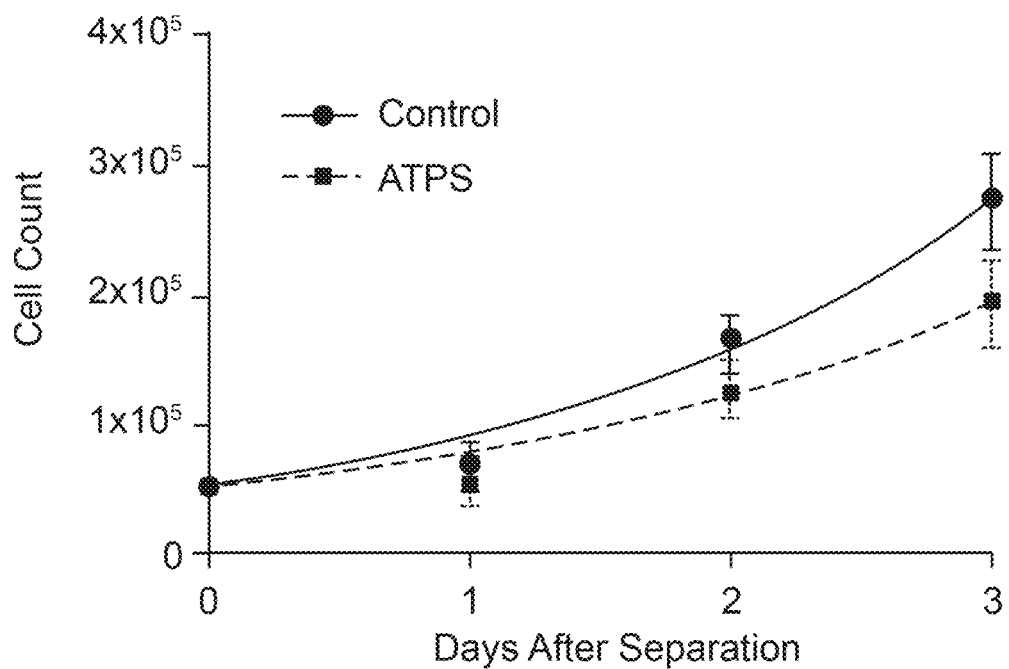
FIG. 4A is a plot showing a data fit of an exponential growth curve for recovered HeLa cells.
Figure 4B:
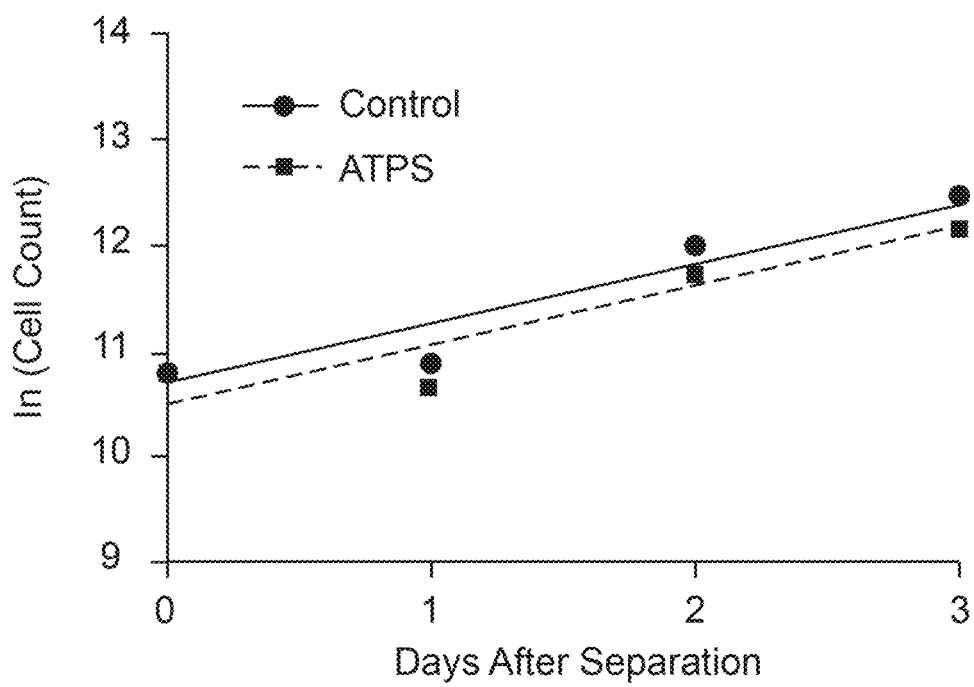
FIG. 4B is a plot showing a natural log (ln) of cell counts vs. days after separation.

Growth curves for HeLa cells were generated by plotting cell count vs. time for 3 days after initial seeding and compared the growth rates of the control population to the recovered cells (FIG. 4B). The control curve represents the average from 4 biological replicates (N=12 total measurements), while the ATPS curve represents an average of 4 biological replicates, which are each the average of 3 technical replicates. Curves for individual biological replicates can be found in the Supporting Information (FIGS. 13A-13D). The population doubling times for the control and recovered populations were 1.08 days and 1.55 days, respectively. These rates were calculated from the exponential growth curve fit to the data. To determine if the growth rates were significantly different, the natural log (ln) of cell count was plotted vs. days of growth. The slope of this curve is the rate constant. The control and ATPS-treated populations were plotted (FIG. 4B) and their slopes, and therefore their growth rates, were found to be only slightly significantly different from each other (p value=0.04). Similar experiments with HL-60 II cells resulted in growth rates (0.70 days and 0.72 days) that were not a statistically different (p-value=0.6). This data is plotted in FIG. 18A and FIG. 18B. Growth rates indicate that the polymers did not significantly alter the cells' behavior in culture, highlighting the biocompatibility of this procedure.

Enrichment of Viability

Cell cultures may become contaminated with nonviable cells either as the result of an experiment (e.g., in vitro cytotoxicity assay) or due to neglect and overgrowth. These cells will typically have a different density than the general population due to loss of osmotic control or total lysis. Because of this difference in density, the disclosed method can be used to enrich the population for viable cells. To demonstrate this application of the presently disclosed ATPS, overgrown cultures of HeLa cells were used with high numbers of nonviable cells. Cells suspended in the medium of the overgrown culture had an average viability of 7.2%, while overgrown cells adhered to the dish had an average viability of 47.4%. After treatment with the presently disclosed ATPS, cells recovered from the interface had an average viability of 66.8% (N=3 technical replicates containing 3 biological replicates each) indicating that the presently disclosed ATPS enriches the viability of overgrown cells by an average of 40.9% (see FIG. 5). This data shows that the presently disclosed ATPS can be used to enrich the viability of neglected cells, and that treatment with the presently disclosed ATPS significantly increases viability of cell populations. Tests for each of the 3 trials indicate a significant difference between ATPS-enriched and control populations with p values of 0.002, <0.001, and <0.001 in trials 1, 2, and 3, respectively.

Decontamination of HeLa Cultures

The effectiveness of the separation and the ability of the system to remove contamination was tracked using fluorescence microscopy (see FIGS. 6A-6D), flow cytometry, and CFU counts (see FIG. 7). Suspensions of cells were analyzed after three separation trials for the presence of total bacteria as well as HeLa cell-bacteria aggregates by flow cytometry. Cell-bacteria aggregates were identified as cell-sized particles that were positive for both red and green fluorescence. Total bacteria was identified as any particle that was positive for red fluorescence.

Additionally, colony formation assays were performed to quantify the amount of active bacteria remaining in the culture following treatment. For the first two trials, the presently disclosed ATPS considerably reduced the bacteria present in the suspension, decreasing the CFU by an average of 70%. In these two trials, the ATPS also reduced the cell-bacteria aggregates by an average of 47% and the total number of bacteria by an average of 37%, as determined by flow cytometry. In trial 3 however, there were 11% more bacteria in the treated suspension than the control, while the system reduced the cell-bacteria aggregates by only 5% and the total number of bacteria by 8%. The three technical replicates were reproducible within each of the three biological replicate trials.

The inconsistency in the outcomes among these three trials highlights inherent differences expected of biological replicates. Ideally, the method would remove all of the detectable bacteria from the culture, but it may not be necessary. Significantly reducing the bacteria count in the culture can increase the effectiveness and reduce the required duration of antibiotic treatment. To test the success of post-separation antibiotic treatment, a fourth contaminated culture was generated and treated it with our ATPS separation method. This suspension of cells, which had 84% less CFU after treatment (see FIG. 8), was used to seed a new culture with and without penicillin/streptomycin antibiotics. These cultures were grown for 3 days and then re-evaluated by colony formation assay. No bacteria was detectable after this brief antibiotic treatment. This result indicates that absent 100% separation efficiency, the ATPS can still be used in conjunction with other treatments to recover the desired cells.

Conclusions

The work described above discloses a method for density-based separation of desired mammalian cells from contaminants in culture including microorganisms and nonviable cells. Separation was achieved using a PEG-Ficoll ATPS whose physical properties were characterized and tuned to ensure biocompatibility. This method could be useful in laboratory settings where cell cultures have become contaminated or overpopulated with nonviable cells and researchers wish to attempt to save the cultures rather than simply dispose of them. The ATPS separation can be used to reduce the amount of contaminants considerably in most cases. In the event that the separation is unsuccessful, as was the case in one of the trials, the cells can still be disposed of or treated with antibiotics. Thus, this method is a low risk, high reward option in instances where the contaminated cells are of particularly high value.

In alternative embodiments, ATPS may be optimized to remove bacteria adhered to the mammalian cells and improve on separation efficiency through further manipulation of the physical (e.g., density, osmolality, interfacial tension) and chemical properties (i.e., polymer identities, concentrations, contaminant binding affinities) of the system, or by altering the protocol (e.g., number of wash steps, centrifugation speeds, and number of passes through the ATPS). The sharp, thermodynamically stable, and potentially biocompatible density step at the liquid-liquid interface of ATPS allows the exploiting of inherent differences in densities between desired cell populations and a wide array of potential contaminants. In addition to *E. coli* and nonviable cells, ATPS can be potentially developed to eliminate any contaminant whose density is different from the cultured cells including other bacteria, *mycoplasma*, yeast, and mold.

Adhesion of *E. coli* to HeLa

Figures 14A, 14B, 14C:
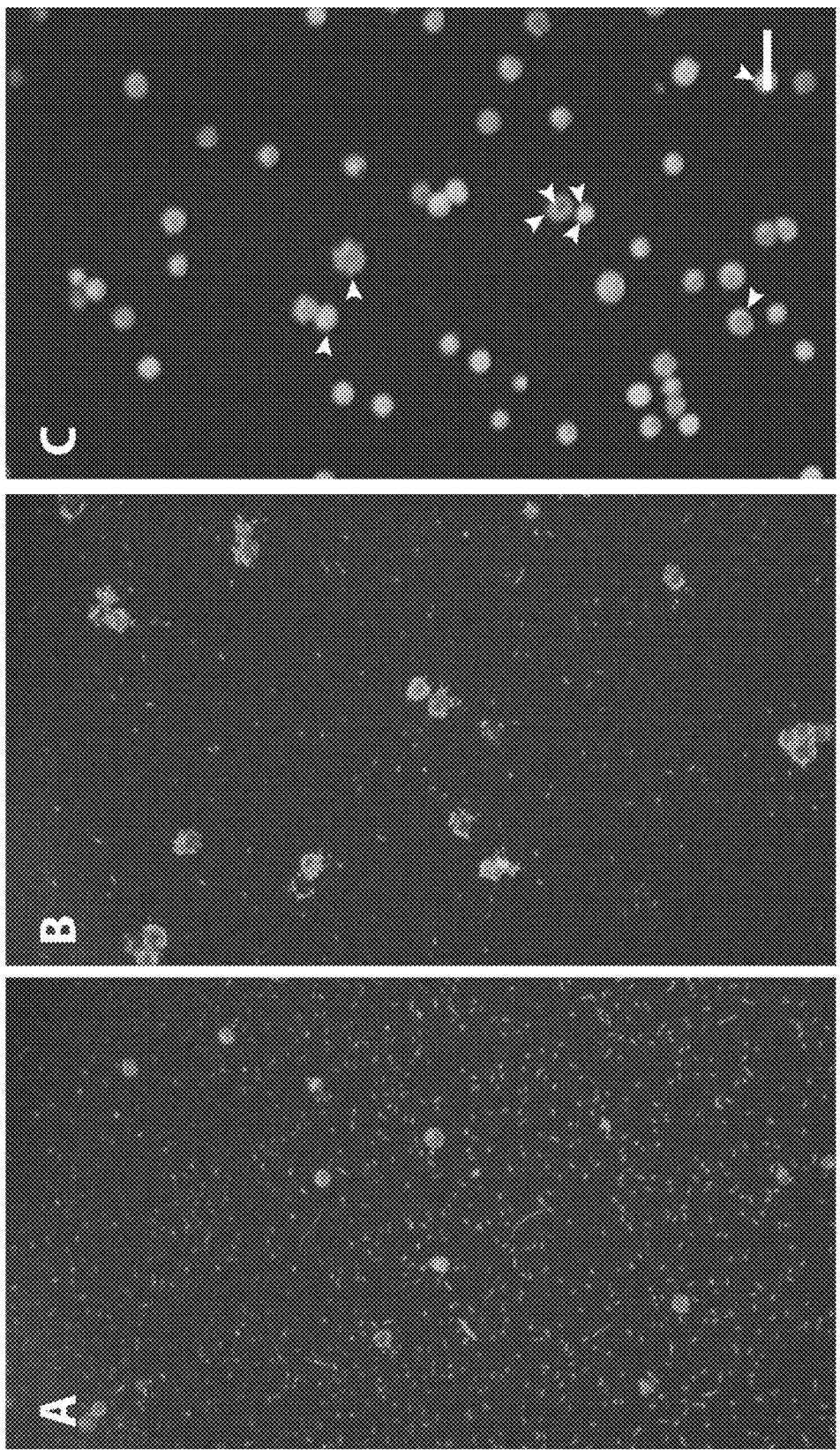
FIG. 14A shows a representative image of *E. coli* initially spiked into GFP-HeLa cultures.
FIG. 14B shows a representative image of adherence of *E. coli* to HeLa cells after 15 minutes of incubation.
FIG. 14C shows a representative image after the passing of cells through a PEG-Ficoll ATPS.

Recovered cell populations contain HeLa cells that had *E. coli* adhered to their surfaces (see FIGS. 14A-14C). This adhesion is likely responsible for most of the *E. coli* that were still present in the recovered cell population because free *E. coli* would have sedimented to the container-ATPS interface based on density alone. Suspensions of HeLa cells that had recently been spiked with bacteria showed little to no bacterial adhesion, but cells incubated with bacteria for >15 minutes showed the formation of bacteria-cell aggregates. Cultures that had been incubated for >30 minutes were used because these bacteria-cell aggregates more accurately reflect real-world contamination.

To enhance separation efficiency, attempts were made to remove the *E. coli* from the HeLa cells prior to adding them to the ATPS by washing them in various solutions. These solutions included surfactants (e.g., Pluronic F68, Jeffamine, Tween-20), blocking agents (skim milk), sugars (mannose and sialic acid) and ethylenediaminetetraacetic acid (EDTA). Attempts were also made to remove the bacteria through physical (e.g., sonication, increased centrifugation speed) and enzymatic means (trypsin). The step in density in the ATPS was adjusted to a lower density to pass cell aggregates through the system based on their increase in density in comparison to free HeLa cells. The suspension was also passed through the system more than once. None of these methods eliminated adhered bacteria from the recovered cell population. We observed the same phenomenon with other adherent cell lines (3T3-L1, INS-1, MCF-7, and MDA-MB-231) and suspension cell lines (HL-60 and Jurkat D1.1).

Image Processing

Images were imported from microscopy software (Andor iQ3) as .tiff files and as .png files showing the overlay of GFP and RFP filters. The images were opened in Adobe Photoshop and the brightness and contrast were enhanced using the "Auto" feature. Images were compiled, sized, and marked up using Adobe Illustrator.

Illustrations

Referring to FIG. 1A, a cell culture decontamination procedure uses ATPS, with a first step (1) having a contaminated culture of adherent cells identified through discolored, cloudy culture medium, and a second step (2) having the contaminated medium removed and the plate washed with buffer, which reduces the number of bacteria. In a third step (3) the cells are trypsinized and resuspended in fresh medium, and in a fourth step (4) 1 mL of this contaminated cell suspension is carefully layered on the top phase of a prepared ATPS. In a fifth step (5) the ATPS is centrifuged for 15 minutes at 2000 g, causing the contaminants to sediment to the bottom of the tube and the cells to collect at the liquid interface. In a sixth step (6) the top phase is removed and the 2 mL surrounding and including the interface is transferred by pipette into 3 mL of fresh medium, and, in a seventh step (7) and an eighth step (8), leaving the bottom phase and contaminants to be discarded. In a ninth step (9) the cell suspension is washed with medium to remove phase-forming components, and, in a tenth step (10), resuspended in fresh medium to be cultured. Finally, in an eleventh step (11) the decontaminated cell suspension is seeded in a new culture and monitored for the recurrence of contamination.

In the procedure generally described above, the method is directed to an aqueous multiphase system 100 in which contaminants 102 are separated from mammalian cells 104. In step (3), a container 106 in the form of a tube is loaded with a liquid 108 having a top liquid phase 110 that is separated from a bottom liquid phase 112 at a liquid-to-liquid interface 113. The top liquid phase 110 has a top liquid density that is different than a bottom liquid density of the bottom liquid phase 112. The container 106 has a top open end 114 and a bottom closed end 116. Optionally, the bottom closed end 116 is tapered.

A cover medium 118 is inserted into the container 106 in the third step (3), the cover medium 118 including a mixture of the cultured mammalian cells 104 and the contaminants 102. The mixture remains initially in a mixed form during a first time period, e.g., prior to the fifth step (5). The cultured mammalian cells 104 have a cell density and the contaminants 102 have a contaminant density, the cell density being different than the contaminant density.

The container 106 is centrifuged in the fifth step (5) for a second time period subsequent to the first time period. In response to the centrifuging and in accordance with the respective density, the cultured mammalian cells 104 are separated from the contaminants 102, with the cultured mammalian cells 104 being located at the liquid-to-liquid interface 113 between the top liquid phase 110 and the bottom liquid phase 112. The contaminants 102 are now, e.g., the eight (8) and ninth step (9), located at the bottom closed end 116 of the container 106.

Figure 1B:
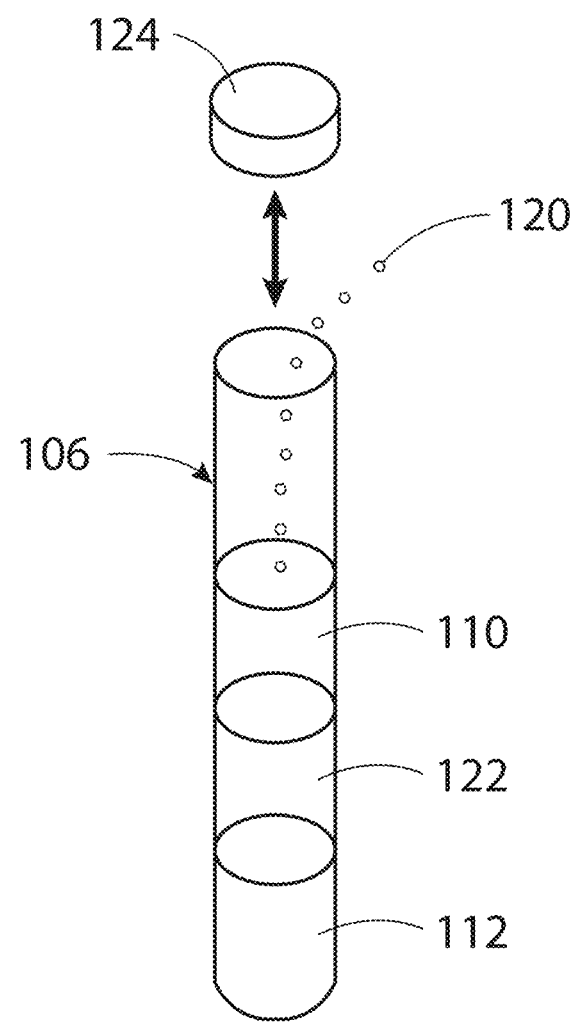
FIG. 1B is a perspective view illustrating a container of the aqueous multiphase system of FIG. 1A.

Referring to FIG. 1B, optionally, a mixture of polymers and salts 120 are added to the liquid 108 to form the top liquid phase and the bottom liquid phase. Optionally, yet, an additional intermediate liquid phase 122 is formed between the top liquid phase 110 and the bottom liquid phase 112, the intermediate liquid phase having an intermediate liquid density that is different than the top liquid density or the bottom liquid density.

According to another optional embodiment, the container 106 includes a cover 124 that is attached to the top open end 116 and that is movable between a closed position in which the top open end 116 is covered and an open position in which the top open end 116 is uncovered.

Referring to FIG. 2, a table shows density, osmolality, and pH values of top and bottom phases of the ATPS. Of note, N=3, with uncertainty reported being standard error of the mean.

Referring to FIG. 3, a table shows a percentage of cells added to the ATPS that are recovered from the interface with their respective viabilities. Each trial represents a biological replicate, which is the average of 3 technical replicates. A single control was analyzed for each trial. Final averages are of all replicates (N=15 for ATPS, N=5 for controls). The uncertainty shown is a standard error of the mean.

Referring generally to FIGS. 4A and 4B, growth curves for HeLa cells are shown after the HeLa cells are recovered from the interface of the ATPS. More specifically, FIG. 4A shows a plot of the data fit to an exponential growth curve. The control curve is the average of four biological replicates (N=12 total). The ATPS curve is an average of four biological replicates, which are each the average of three technical replicates. Error bars represent the standard error of the mean. The data was fit to exponential growth curves for quantitative comparison of growth rate. Referring to FIG. 4B, a plot shows the natural log (ln) of cell counts vs. days after separation were plotted and fit to lines. The slopes of these lines represent the growth rate of the cultures, and were not found to differ significantly (p value=0.5).

Figure 5:
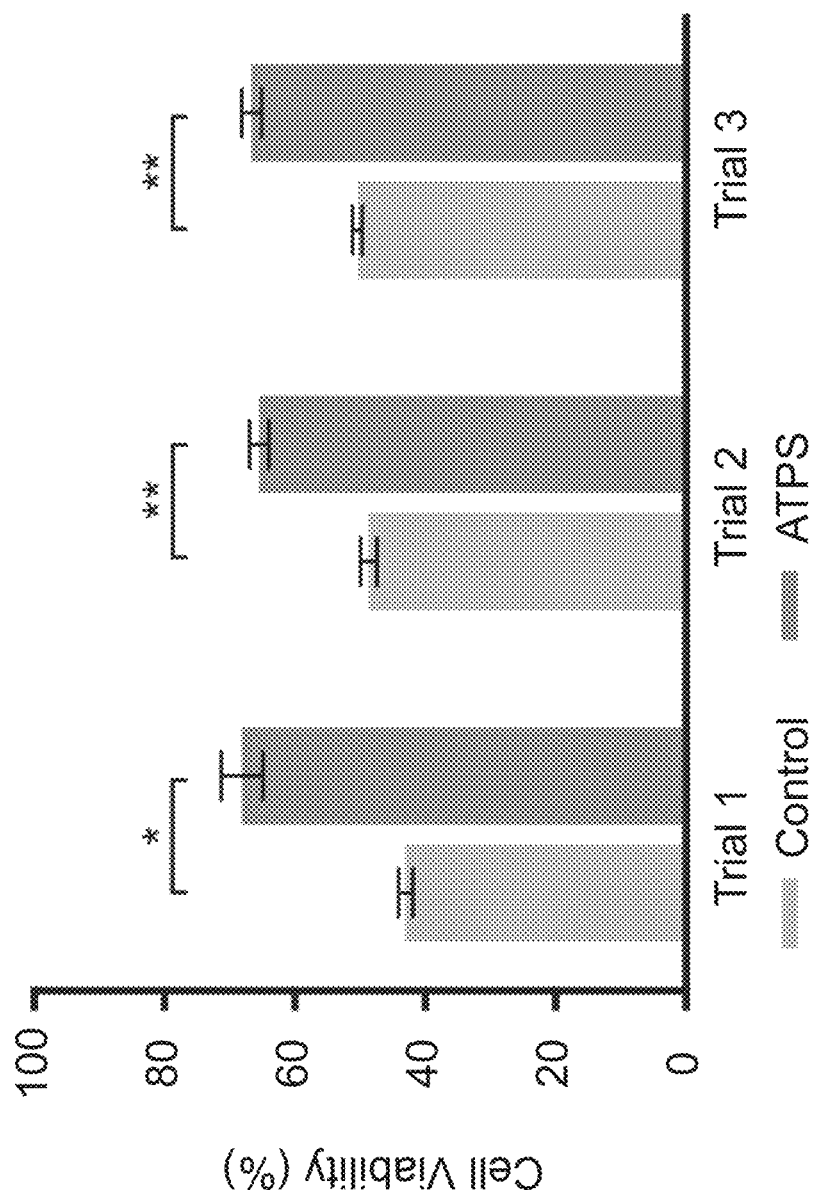
FIG. 5 is a bar chart showing a viability enrichment of overgrown cells upon separation in ATPS.

Referring to FIG. 5, a bar chart shows a viability enrichment of overgrown cells upon separation in ATPS. The viability of overgrown cells was analyzed using propidium iodide dye exclusion and flow cytometry (N=10,000 events). Three biological replicates, each consisting of three technical replicates, were performed. Averages are plotted with error bars representing the standard error of the mean. Student's t-test results indicate significant differences between the viability of control and ATPS-treated populations with p values of =0.002 for trial 1 (*) and <0.001 for trials 2 and 3 (**).

Figure 6A:
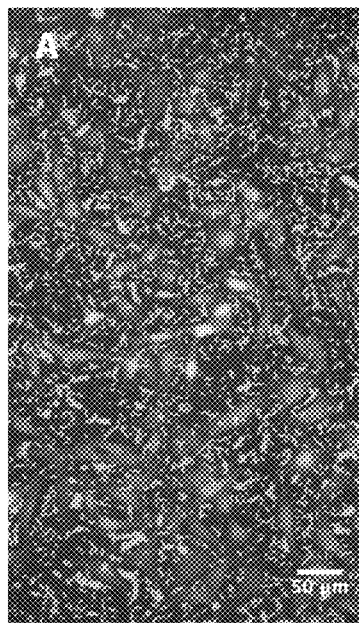
FIG. 6A is a representative image of an initial GFP-HeLa culture after contamination.
Figure 6B:
FIG. 6B is a representative image of the contaminated medium with most of the free bacteria being removed.
Figure 6C:
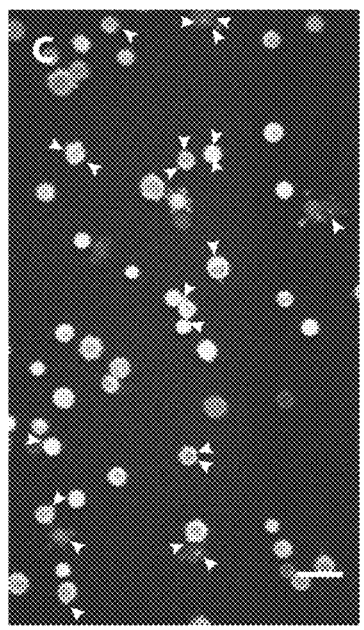
FIG. 6C is a representative image of the positive contaminated population after trypsinization.
Figure 6D:
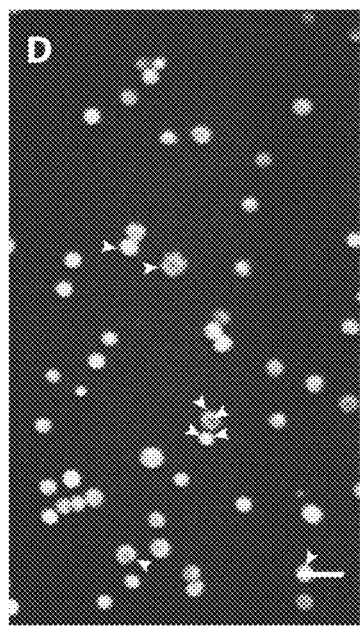
FIG. 6D is a representative image of the contaminated population after being recovered.

Referring generally to FIGS. 6A-6D, selected representative images show major steps in the decontamination procedure. In FIG. 6A, an initial GFP-HeLa culture is shown after contamination with mPlum $E.$ $coli$ and 30 minutes of incubation in L-15 medium. In FIG. 6B, the contaminated medium is aspirated and the plate is washed with 1× PBS to remove most of the free bacteria. In FIG. 6C, the positive control (contaminated) population is shown after trypsinization, which contains several bacteria. In FIG. 6D, the contaminated population is shown after being recovered from the interface of the ATPS, with a reduced number of bacteria present. Arrowheads in FIGS. 6C and 6D mark bacteria. Scale bars in each image (FIGS. 6A-6D) represent 50 μm.

Referring to FIG. 7, a table shows quantitative measurements of the separation efficiency of the PEG-Ficoll ATPS by counts of colony forming units (CFU) and two flow cytometry gating strategies. Flow cytometry results are reported as the percent of total cells that are within the gating parameters for that experiment.

Referring to FIG. 8, a table shows CFU/ml counts for contaminated cell suspensions. ATPS separation reduced CFU count by 84%. Day 3 indicates CFU present after 3 days in culture. Cells cultured with 1% penicillin/streptomycin show zero CFU.

Referring to FIG. 9, a table shows the densities and osmolalties of each phase of a 7% (w/w) PEG—11% (w/w) Ficoll ATPS. The ATPS was prepared with different concentrations of PBS.

Figures 10A, 10B, 10C:
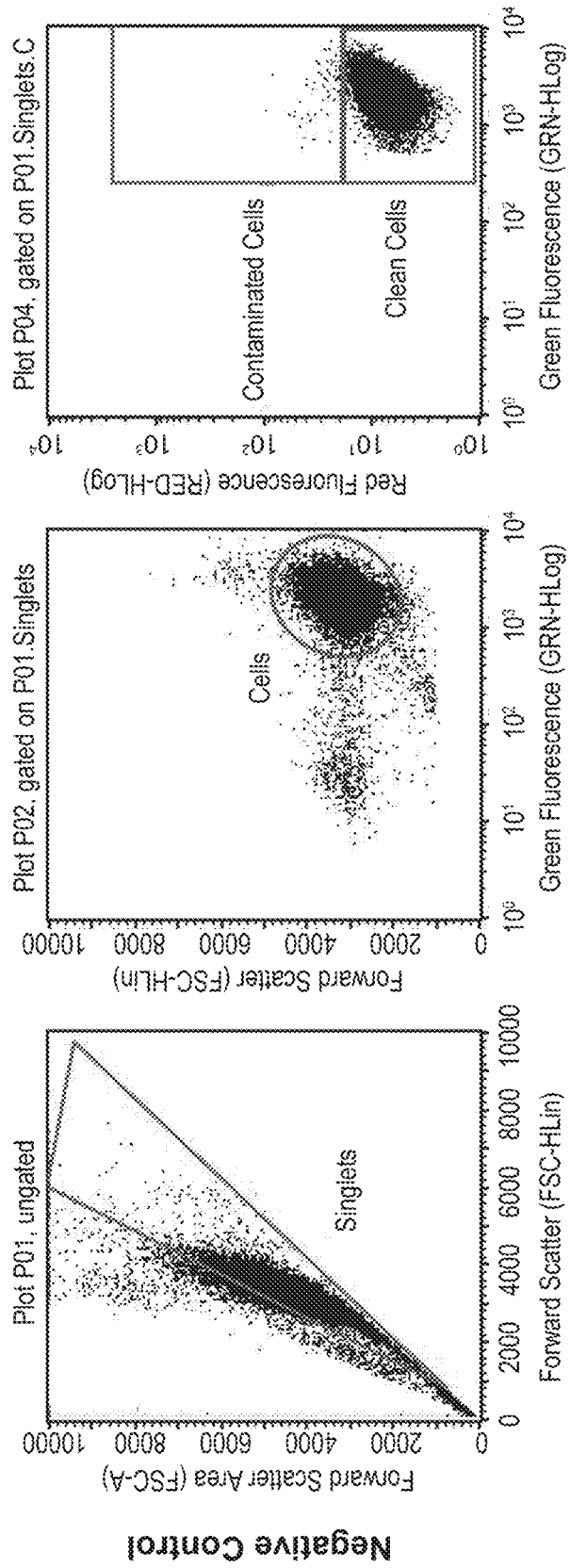
FIG. 10A shows a representative image of flow cytometry data for negative control of singlets.
FIG. 10B shows a representative image of flow cytometry data for negative control of cells.
FIG. 10C shows a representative image of flow cytometry data for negative control of contaminated and clean cells.
Figures 10G, 10H, 10I:
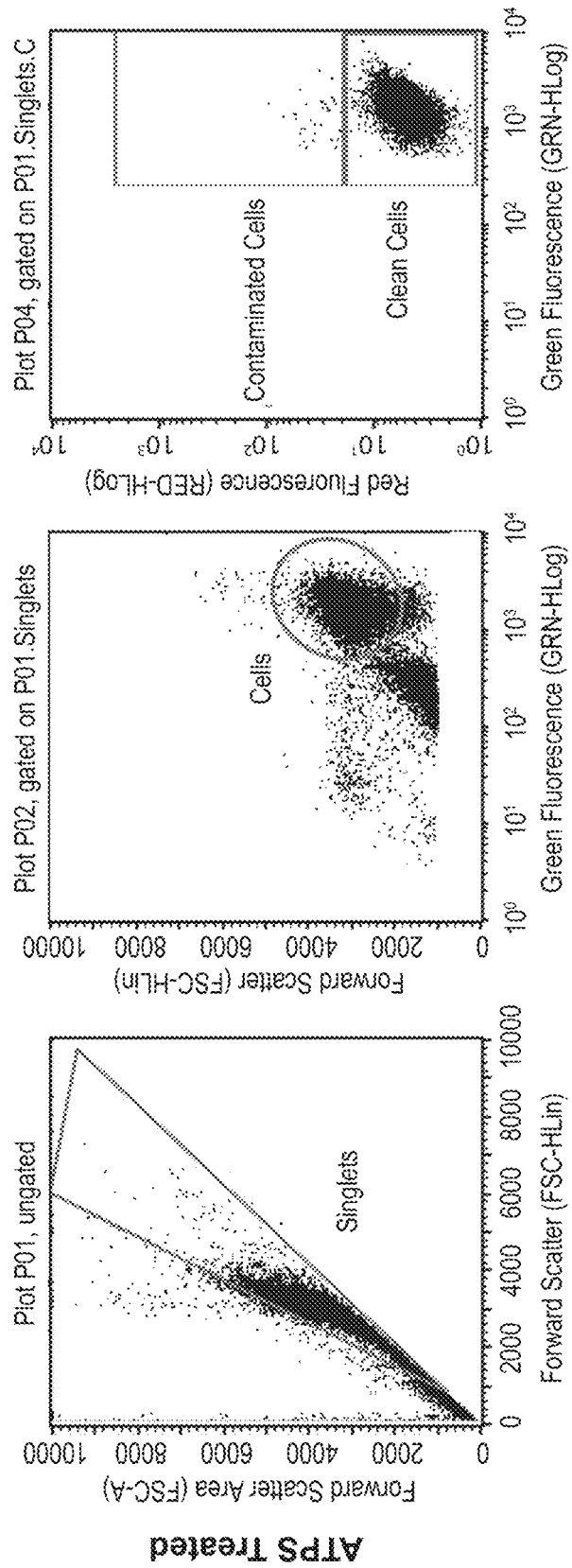
FIG. 10G shows a representative image of flow cytometry data for ATPS-treated sample of singlets.
FIG. 10H shows a representative image of flow cytometry data for ATPS-treated sample of cells.
FIG. 10I shows a representative image of flow cytometry data for ATPS-treated sample of contaminated and clean cells.

Referring to FIGS. 10A-10I, flow cytometry data shows gating strategies for GFP-HeLa cells with mPlum *E. coli* adhered to their surfaces. Representative images show negative control (FIGS. 10A-10C), contaminated positive control (FIGS. 10D-10F), and contaminated ATPS-treated sample (FIGS. 10G-10I).

Referring to FIGS. 11A-11C, flow cytometry data shows gating for total mPlum *E. coli*. Ungated scatter plots were divided into quadrants positive for green fluorescence and for red fluorescence. All events in the two top quadrants were considered bacteria. Representative images of negative control (FIG. 11A), positive (contaminated) control (FIG. 11B), and ATPS treated samples (FIG. 11C) are shown from trial 1.

Figure 12A:
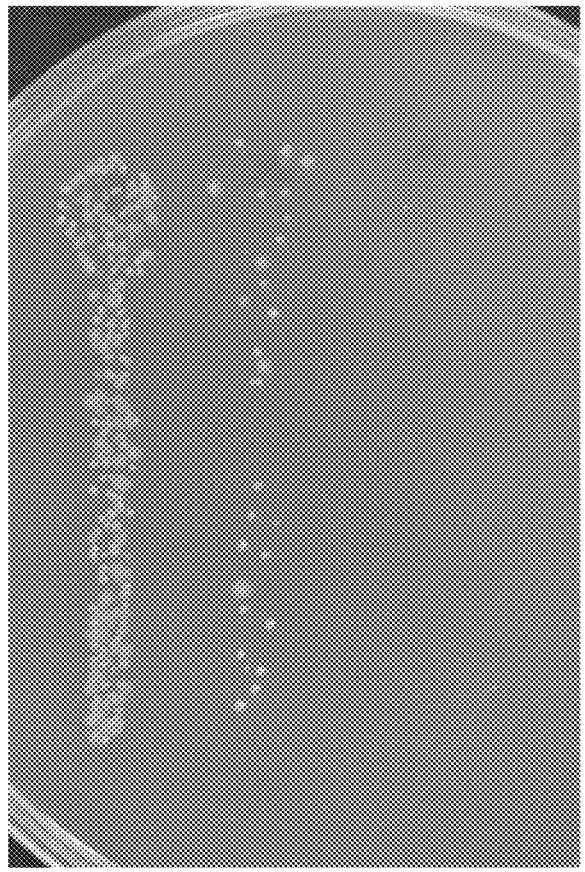
FIG. 12A shows a representative image from a colony formation before treatment with a PEG-Ficoll ATPS.
Figure 12B:
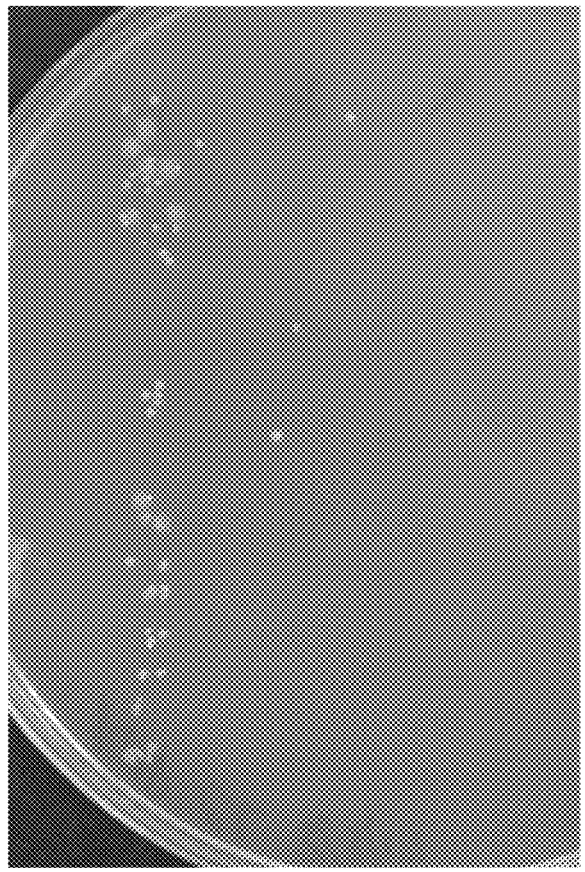
FIG. 12B shows a representative image from a colony formation after treatment with a PEG-Ficoll ATPS.
Figure 12C:
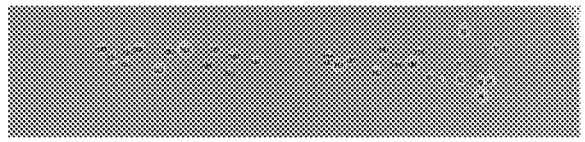
FIG. 12C shows an image with automated identification of individual colonies before treatment with a PEG-Ficoll ATPS.
Figure 12D:
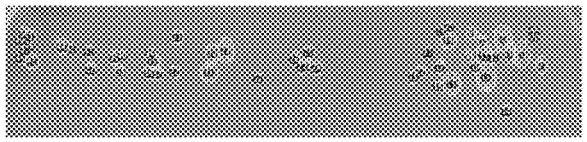
FIG. 12D shows an image with automated identification of individual colonies after treatment with a PEG-Ficoll ATPS.

Referring to FIGS. 12A-12D, colony formation assays are generally illustrated, with representative images in FIGS. 12A and 12B showing a colony formation assay to determine the total colony forming units (CFU)/mL present in contaminated culture of HeLa cells before and after treatment with a PEG-Ficoll ATPS. In FIGS. 12C and 12D, images from ImageJ show automated identification of individual colonies.

Referring to FIGS. 13A-13D, growth curves are shown for individual biological replicates of HeLa cells recovered from the interface of a PEG-Ficoll ATPS. Each biological replicate consists of the average of 3 technical replicates for ATPS-treated cells and a single control. Error bars represent standard error of the mean.

Referring to FIGS. 14A-14C, representative images show time-dependent adherence of *E. coli* to HeLa cells. When mPlum-expressing *E. coli* (generally shown as larger particles) are initially spiked into GFP-HeLa (generally shown as smaller particles) cultures in suspension, there is little to no adhesion (see FIG. 14A). After 15 minutes of incubation (see FIG. 14B), most of the HeLa cells have many bacteria adhered to their surface. After passing cells through a PEG-Ficoll ATPS (see FIG. 14C, which is reproduced generally from data of FIG. 5), there are still several cells with bacteria adhered to their surface in the recovered cell population (as identified via arrow heads).

Referring to FIGS. 15 and 16, improved data generally shows reproducibility of ATPS and a focused study on the reproducibility of density, osmolality, and pH of ATPS. More specifically, referring to FIG. 15, ATPS developed with a top phase density of 1.0433±0.0002 g/mL and a bottom phase density of 1.0755±0.0004 g/mL (N=5, one measurement from each of five separate stock solution preparations), which would allow for the desired separation of HeLa and *E. coli* cells. Several relative concentrations of PEG and Ficoll were evaluated and final concentrations of 7% w/w PEG (8,000 g/mol) and 11% w/w Ficoll (400,000 g/mol) were selected because they produced the desired densities for the cell separation systems. These concentrations produce a system that is 70% top phase 30% bottom phase by volume. PEG 8K was chosen because it allows for sterilization by filtration using 0.22 μm filters, while larger molecular weight PEG does not. To ensure biocompatibility, a range of phosphate buffered saline (PBS) concentrations was tested and it was found that systems prepared in 0.6× PBS yielded a top phase osmolality of 292±3 mOsm/kg, pH 7.38±0.02, and a bottom phase osmolality of 294±4 mOsm/kg, pH 7.38±0.03 (as represented in FIG. 15). This ATPS formulation allows the cells to be separated without adversely affecting their morphology and viability. A focused study was further performed on the reproducibility of ATPS preparation comparing systems produced from single stock polymer solutions (as represented in FIG. 16) to systems from 5 separate stock polymer solutions (as represented in FIG. 15).

Referring to FIG. 17, HL-60 II data of recovery and viability in ATPS is represented and in which recovered HL-60 II cells had an average viability of 95.3±2.2% compared to control cells with a viability of 97.2±1.1. Maximizing viability throughout a separation procedure is essential for maintaining cells in a culture after contaminants are removed. Recovered GFP-HeLa cells have an average viability of 98.0±0.2% compared to control with a viability of 98.4±0.2%. As already mentioned above, recovered HL-60 II cells have an average viability of 95.3±2.2% compared to control cells with a viability of 97.2±1.1 (as represented in FIG. 17). The control population is aliquoted from the same suspension of cells but is not passed through an ATPS. The data of FIG. 17 indicates that subjecting the cells to a decontamination procedure, which includes exposure to polymer solutions, relatively high-speed centrifugation, and several pipetting steps, does not result in a loss of viability relative to control. The average viability of cells passed through ATPS is not significantly different from cells passaged using standard cell culture technique (GFP-HeLa p value=0.3, HL-60 II p value=0.4). Because calculations of seeding densities often rely on cell counts, maximizing viability while eliminating nonviable cells allows for more accurate seeding of subsequent cultures.

Figure 18A:
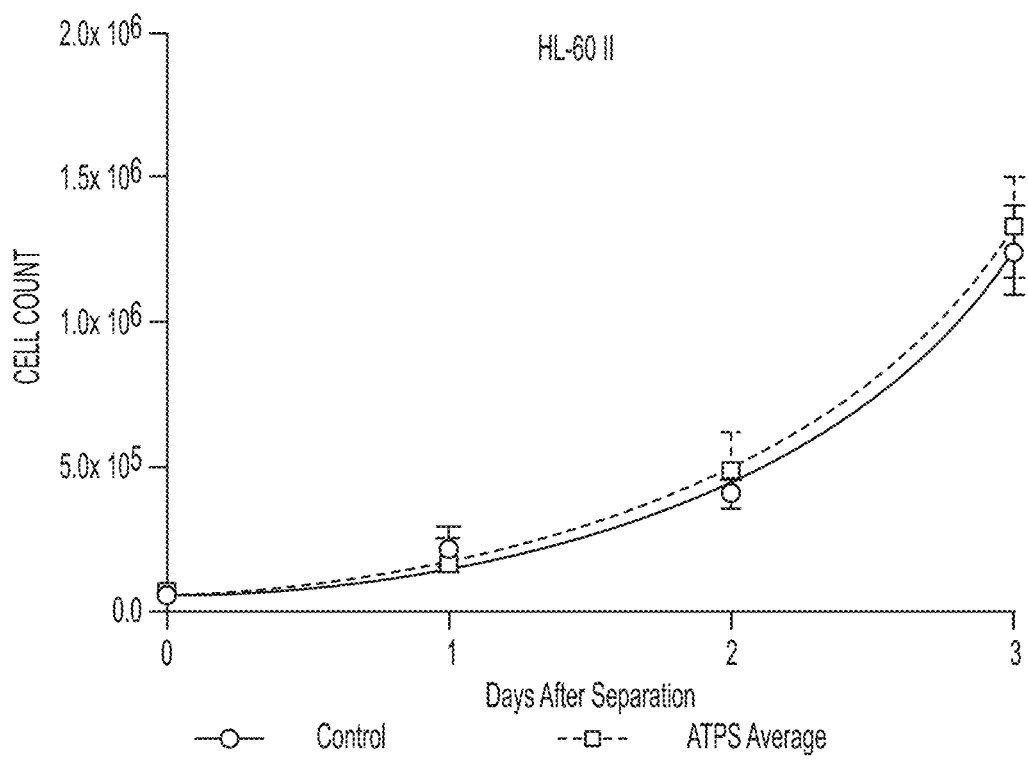
FIG. 18A is a plot showing growth curves for HL-60 II cells before and after being recovered from an interface of ATPS, with cell count data for HL-60 II plotted as a function of days of growth.
Figure 18B:
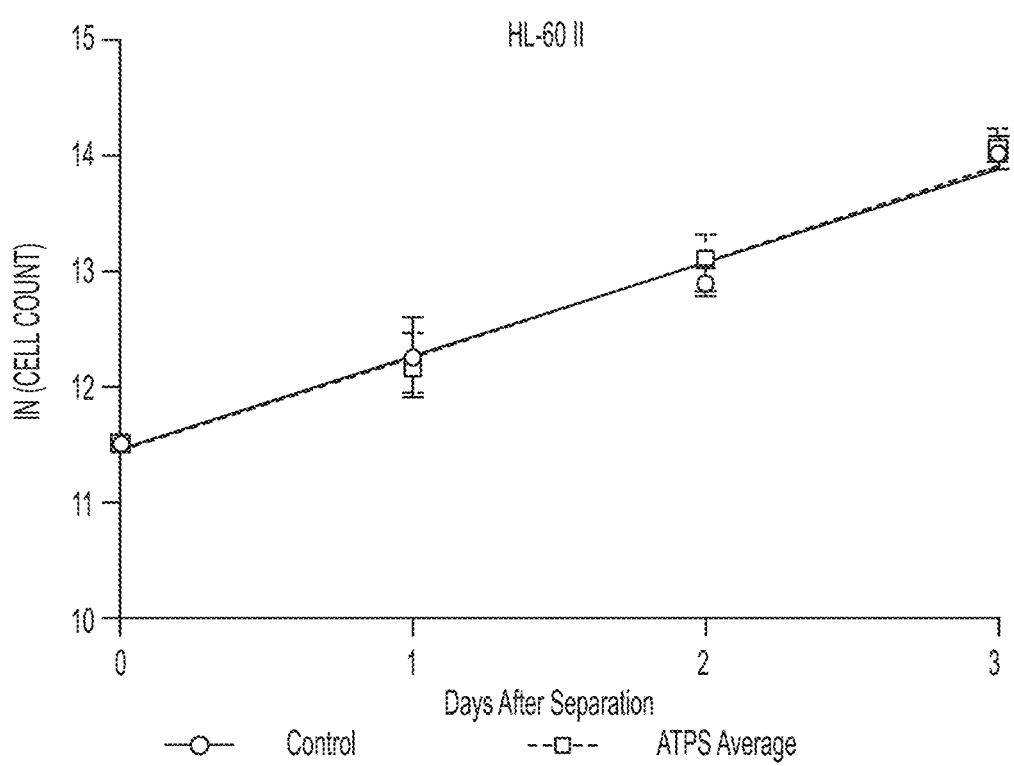
FIG. 18B is a plot showing growth curves for HL-60 II cells before and after being recovered from an interface of ATPS, with the natural log (ln) of cell counts versus days after separation for HL-60 II plotted and fit to lines.
Figure 19A:
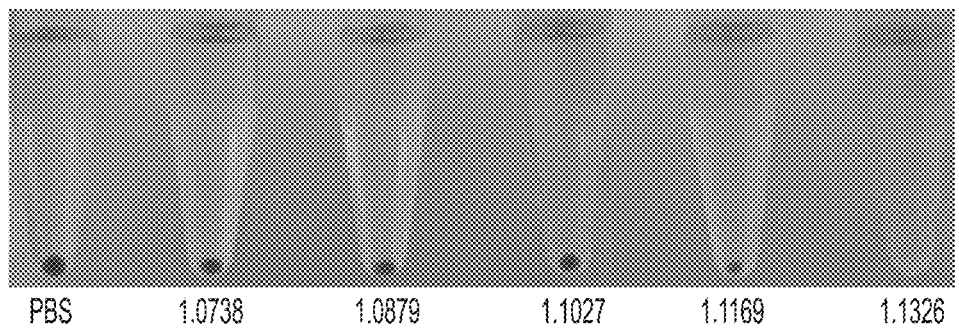
FIG. 19A shows an image in which densities of cells and microorganisms are determined by sink/float assays and in which mPlum *E. coli* cells are used.
Figure 19B:
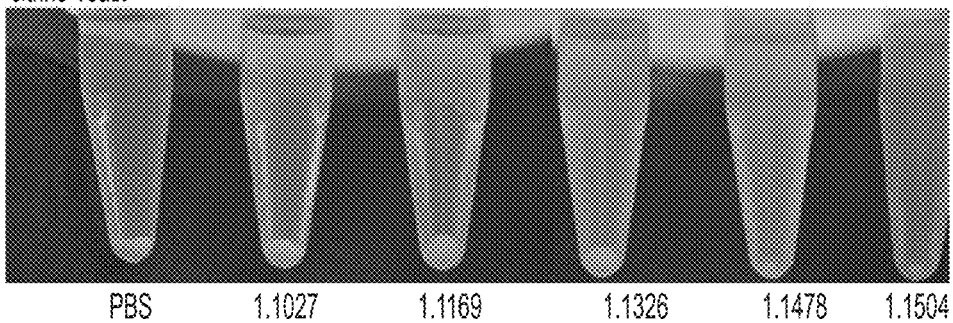
FIG. 19B shows an image in which densities of cells and microorganisms are determined by sink/float assays and in which citrine yeast cells are used.
Figure 19C:
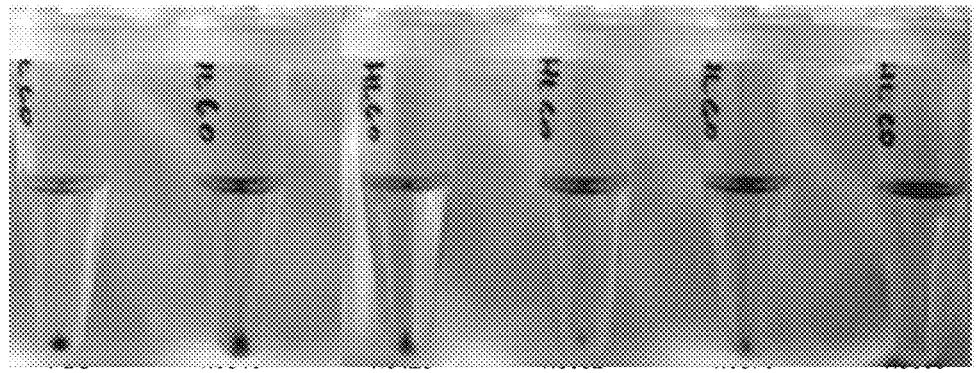
FIG. 19C shows an image in which densities of cells and microorganisms are determined by sink/float assays and in which HL-60 II cells (stained with DiI for contrast) are used.
Figure 19D:
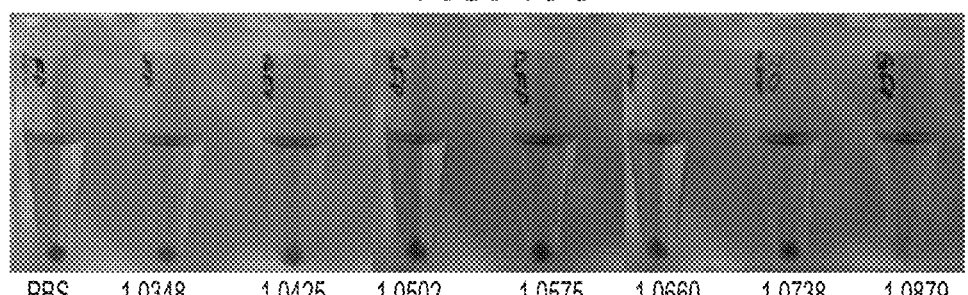
FIG. 19D shows an image in which densities of cells and microorganisms are determined by sink/float assays and in which GFP-HeLa cells (stained with DiI for contrast) are used.
Figure 20A:
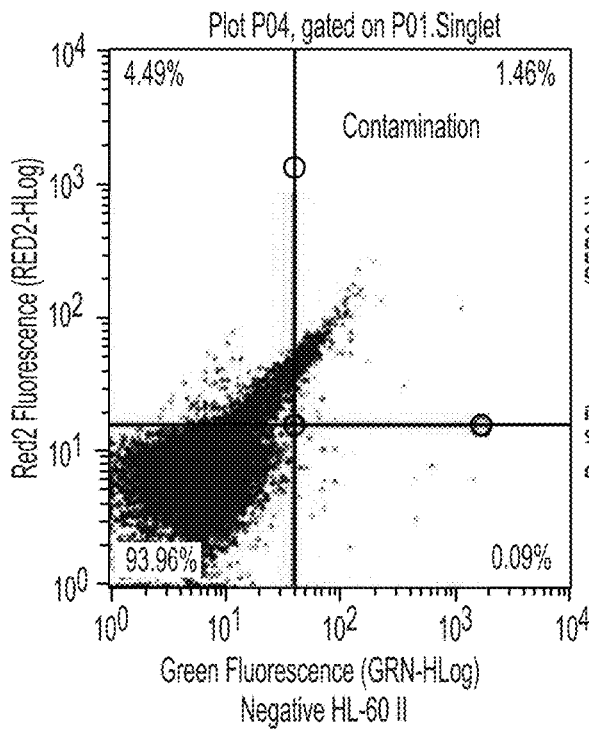
FIG. 20A is a plot showing unstained HL-60 II cells for separation of mPlum *E. coli* from DiO-stained HL-60 II cells experiment.
Figure 20B:
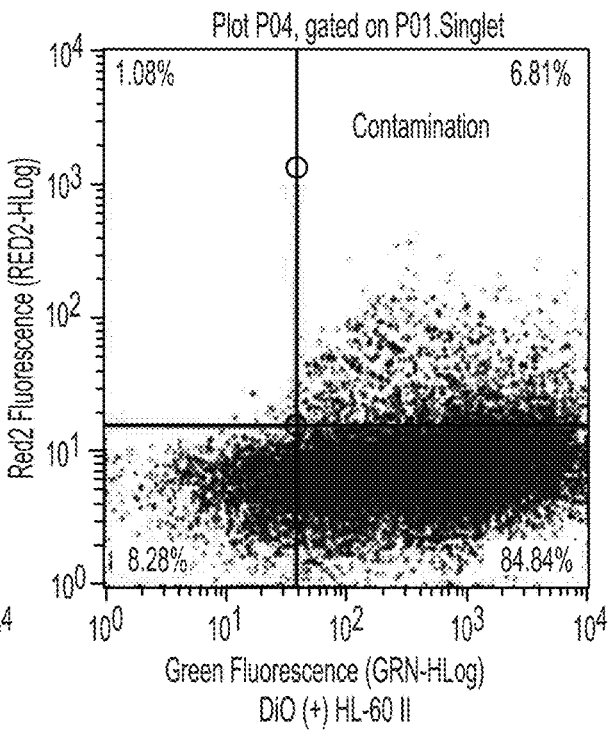
FIG. 20B is a plot showing DiO-stained HL-60 II cells for separation of mPlum *E. coli* from DiO-stained HL-60 II cells experiment.
Figure 20C:
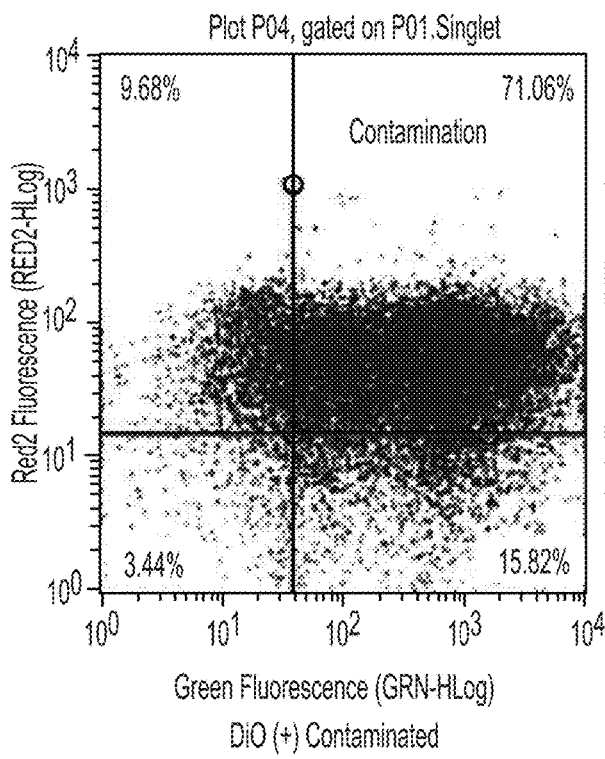
FIG. 20C is a plot showing DiO-stained HL-60 II cells and mPlum *E. coli* for separation of mPlum *E. coli* from DiO-stained HL-60 II cells experiment.
Figure 20D:
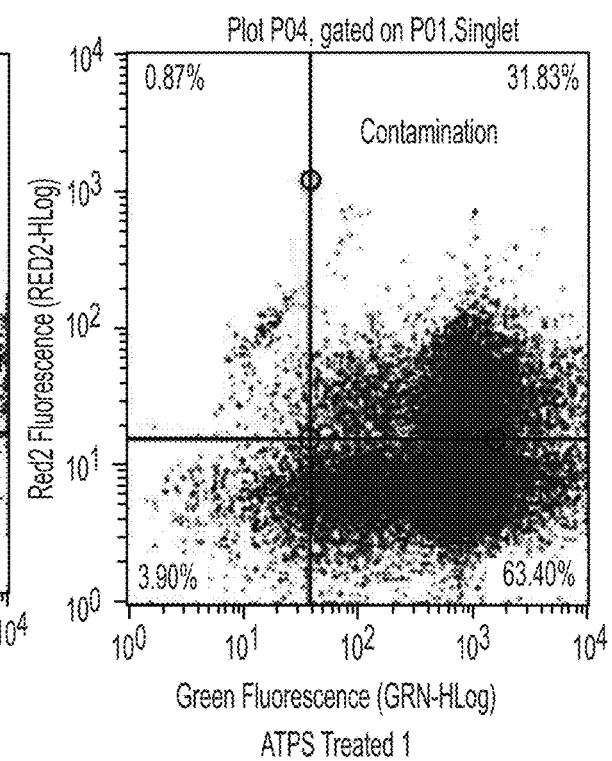
FIG. 20D is a plot showing replicate 1 of ATPS-treated cells for separation of mPlum *E. coli* from DiO-stained HL-60 II cells experiment.
Figures 20E, 20F:
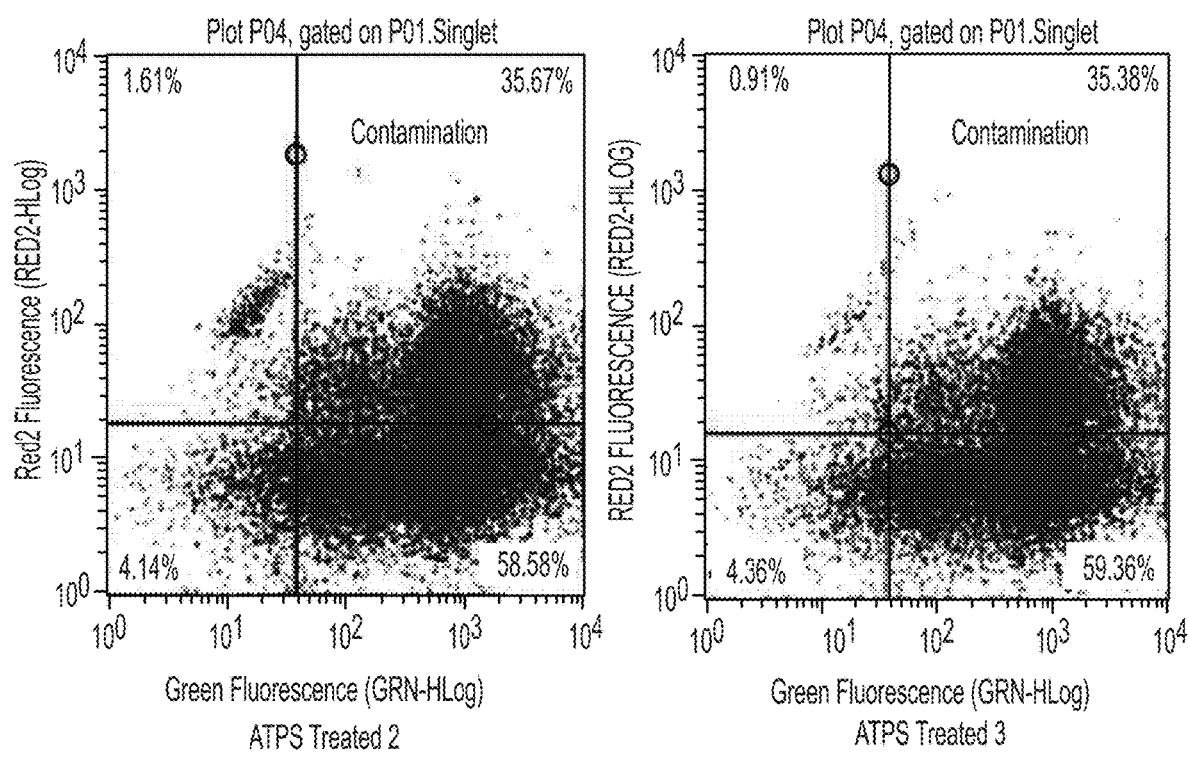
FIG. 20E is a plot showing replicate 2 of ATPS-treated cells for separation of mPlum *E. coli* from DiO-stained HL-60 II cells experiment.
FIG. 20F is a plot showing replicate 3 of ATPS-treated cells for separation of mPlum *E. coli* from DiO-stained HL-60 II cells experiment.
Figure 21A:
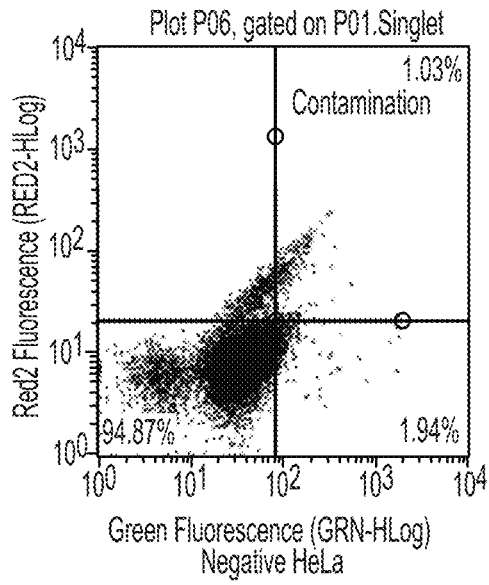
FIG. 21A is a plot showing unstained HeLa cells for separation of citrine-expressing yeast from DiI-stained HeLa cells experiment.
Figure 21B:
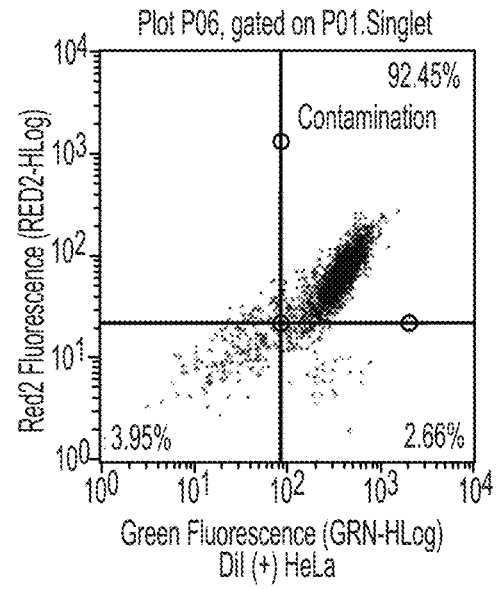
FIG. 21B is a plot showing DiI-stained HeLa cells for separation of citrine-expressing yeast from DiI-stained HeLa cells experiment.
Figure 21C:
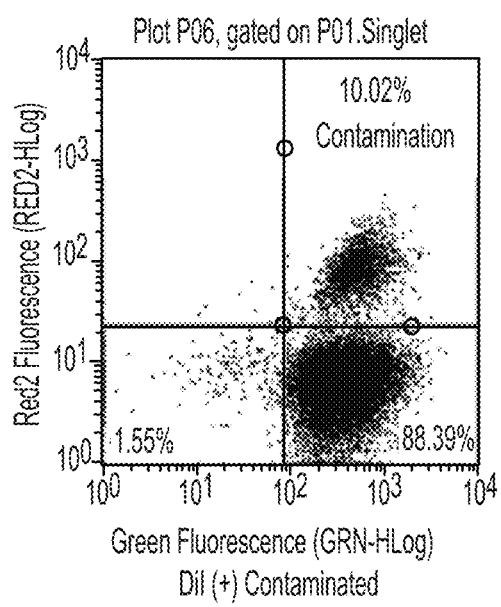
FIG. 21C is a plot showing DiI-stained HeLa cells with citrine-expressing yeast for separation of citrine-expressing yeast from DiI-stained HeLa cells experiment.
Figure 21D:
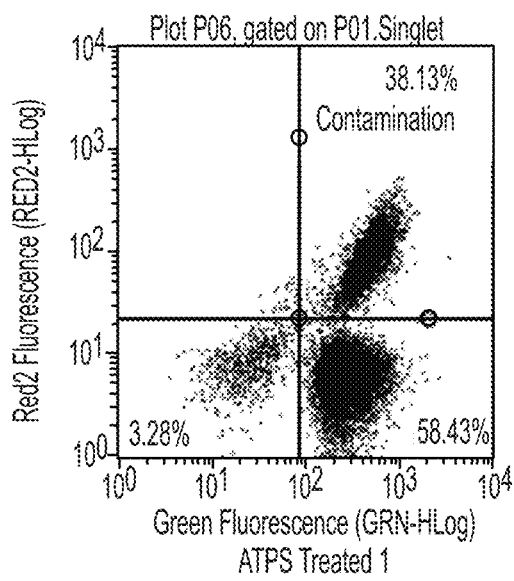
FIG. 21D is a plot showing replicate 1 of ATPS-treated cells for separation of citrine-expressing yeast from DiI-stained HeLa cells experiment.
Figure 21E:
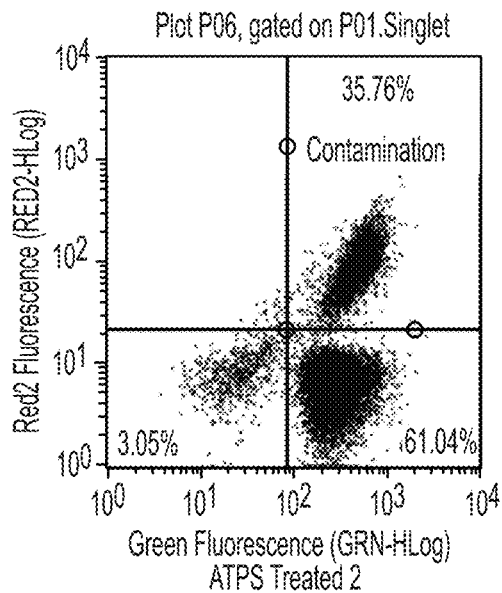
FIG. 21E is a plot showing replicate 2 of ATPS-treated cells for separation of citrine-expressing yeast from DiI-stained HeLa cells experiment.
Figure 21F:
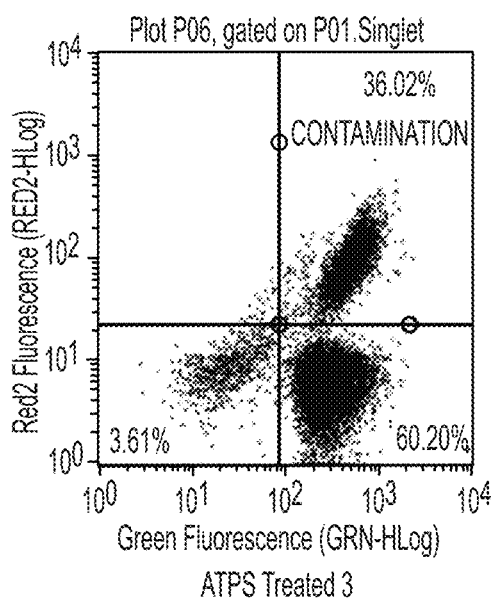
FIG. 21F is a plot showing replicate 3 of ATPS-treated cells for separation of citrine-expressing yeast from DiI-stained HeLa cells experiment.
Figure 21G:
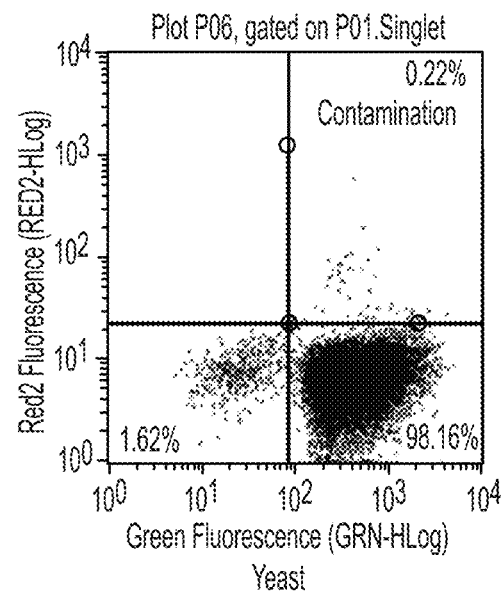
FIG. 21G is a plot showing citrine-expressing yeast for separation of citrine-expressing yeast from DiI-stained HeLa cells experiment.
Figure 22A:
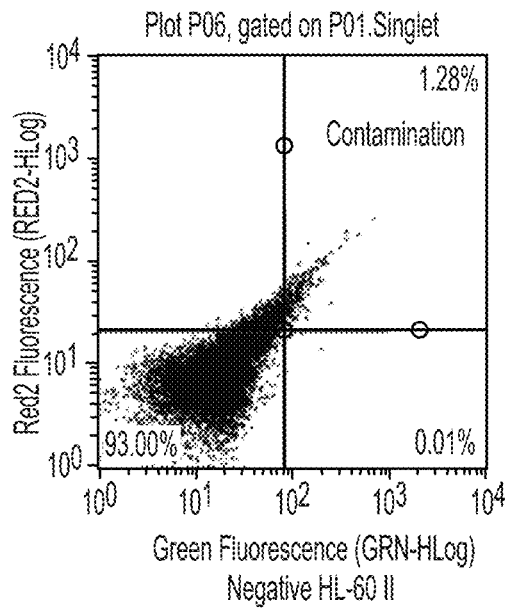
FIG. 22A is a plot showing unstained HL-60 II cells for separation of citrine-expressing yeast from DiI-stained HL-60 II cells experiment.
Figure 22B:
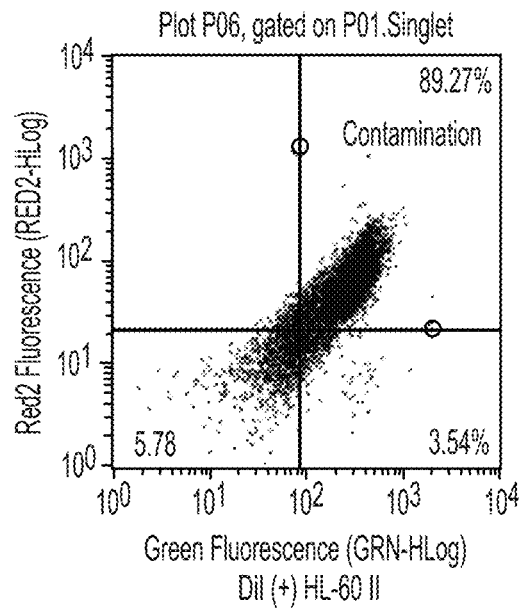
FIG. 22B is a plot showing DiI-stained HL-60 II cells for separation of citrine-expressing yeast from DiI-stained HL-60 II cells experiment.
Figure 22C:
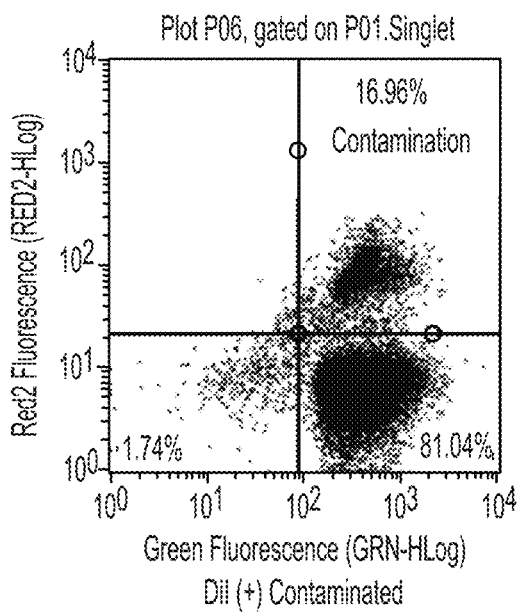
FIG. 22C is a plot showing DiI-stained HL-60 II cells with citrine-expressing yeast for separation of citrine-expressing yeast from DiI-stained HL-60 cells experiment.
Figure 22D:
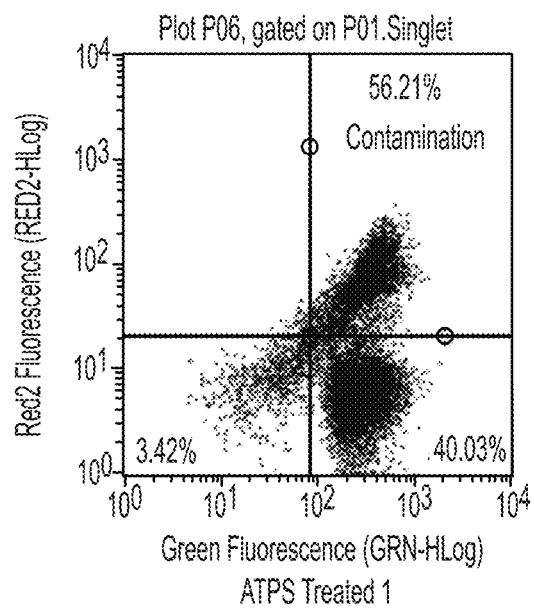
FIG. 22D is a plot showing replicate 1 of ATPS-treated cells for separation of citrine-expressing yeast from DiI-stained HL-60 cells experiment.
Figure 22E:
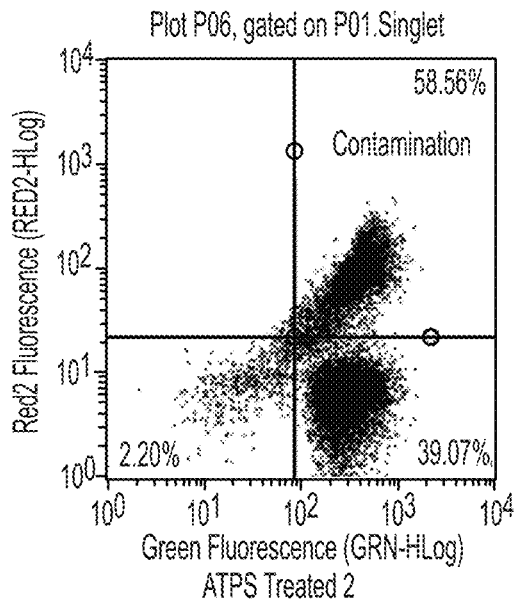
FIG. 22E is a plot showing replicate 2 of ATPS-treated cells for separation of citrine-expressing yeast from DiI-stained HL-60 cells experiment.
Figure 22F:
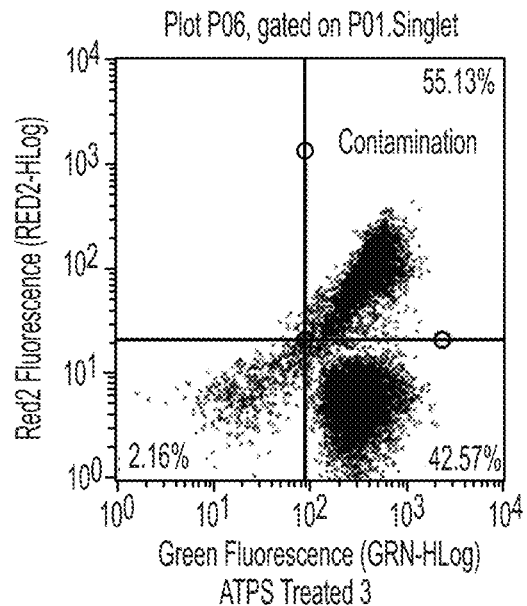
FIG. 22F is a plot showing replicate 3 of ATPS-treated cells for separation of citrine-expressing yeast from DiI-stained HL-60 cells experiment.
Figure 22G:
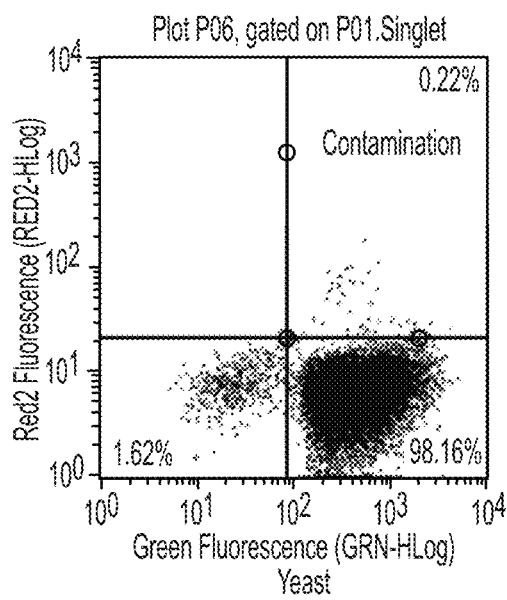
FIG. 22G is a plot showing citrine-expressing yeast for separation of citrine-expressing yeast from DiI-stained HL-60 cells experiment.

Referring to FIGS. 18A and 18B, growth curves for HL-60 II cells are illustrated before and after recovery from the interface of the ATPS. Cell count data for HL-60 II is illustrated in FIG. 18A and is plotted as a function of days of growth. The control curve is the average of 4 biological replicates. The ATPS curve is an average of 4 biological replicates, which are each the average of 3 technical replicates (N=12 total). Error bars represent the standard error of the mean. The data is fit to exponential growth curves for quantitative comparison of growth rate. The natural log (ln) of cell counts vs. days after separation for HL-60 II, as illustrated in FIG. 18B, is plotted and fit to lines. The slopes of these lines represent the growth rate of the cultures, and were not found to differ significantly for HL-60 II (p value=0.6).

Referring to FIGS. 19A-19D, densities of cells and microorganisms were determined by sink/float assays in an experimental study. Nycoprep was diluted to various concentrations to prepare a series of solutions with densities close to the reported densities of the cells and microorganisms used in the experimental study. Cells were added to microcentrifuge tubes and centrifuged. The solutions were inspected for the presence of cells pelleted at the bottom, which would indicate that the density of the cell population was above that of the solution. HL-60 II and GFP-HeLa cells were stained with DiI to aid visualization of the cell pellet. Density ranges found using this sink/float method generally agree with values reported in the literature.

Referring to FIGS. 20A-20F, a separation of mPlum *E. coli* from DiO-stained HL-60 II cells is represented. Cell populations are first gated for single cells and then divided into quadrants that are positive for each of the fluorophores present. Controls show the positions of unstained cells, stained cells, and contaminated cells. Treat cell populates are enriched for HL-60 II cells, removing 58% of the contaminants on average.

Referring to FIGS. 21A-21G, a separation of citrine-expressing yeast from DiI-stained HeLa cells is represented. Cell populations are first gated for single cells and then divided into quadrants that are positive for each of the fluorophores present. Controls show the positions of unstained cells, stained cells, and contaminated cells. Treat cell populates are enriched for HeLa cells, removing 32% of the contaminants on average.

Referring to FIGS. 22A-22G, a separation of citrine-expressing yeast from DiI-stained HL-60 II cells is represented. Cell populations are first gated for single cells and then divided into quadrants that are positive for each of the fluorophores present. Controls show the positions of unstained cells, stained cells, and contaminated cells. Treat cell populates are enriched for HL-60 II cells, removing 50% of the contaminants on average.

Figure 23:
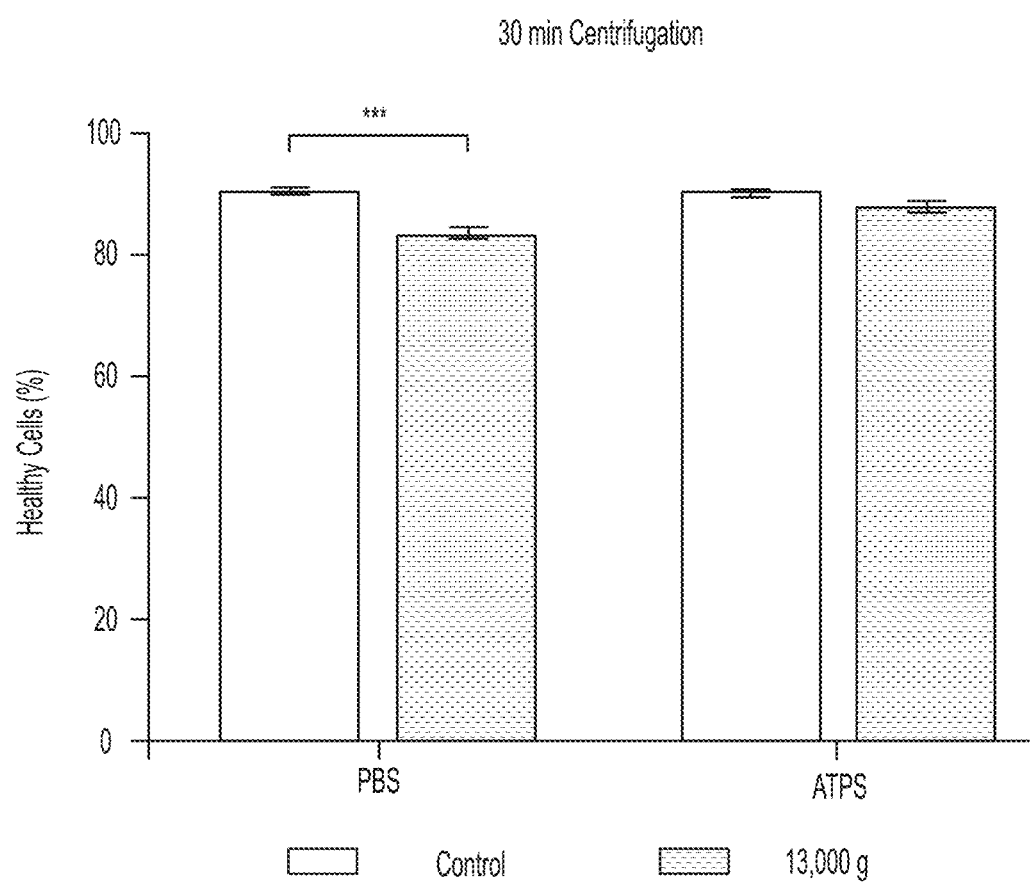
FIG. 23 is a graph showing the viability of HeLa cells centrifuged at 13,000 g for 30 minutes in PBS in comparison to HeLa cells centrifuged at 13,000 g for 30 minutes upon separation in an ATPS.

Referring to FIG. 23, a graph represents HeLa cells centrifuged at 13,000 g for 30 minutes in PBS and which have a small but statistically significant loss in healthy population after recovery. In this experiment, healthy cells were defined as staining negative for Annexin-V (a measure of apoptosis) and propidium iodide (a measure of membrane integrity). Cells that were centrifuged for the same amount of time and at the same speed in the ATPS showed no significant loss in healthy population upon recovery from the liquid-liquid interface. According to other experimental studies, the application has also been tested on more delicate cell types, including bovine mesenchymal stem cells, primary human white blood cells, and suspension cells from established cell lines (HL-60 II, Jurkat D1.1).

According to studies described above, tests were performed for broader applicability using HL-60 II cells (a human promyelocytic leukemia suspension cell line) as a second mammalian cell type and yeast (*S. cerevisiae*) as a second microorganism contaminant. Thus, applicability of above-described system to other cultures and contaminants was studied. Generally, an exemplary study was directed to determining if the system, which was specially tuned to enrich HeLa cells from a culture contaminated with *E. coli*, could be more broadly applied to other cell cultures and other contaminants. More specifically, the exemplary study was directed to testing a suspension cell line and yeast contaminants. The results of the exemplary study found that in an HL-60 II culture contaminated with *E. coli*, the system was able to remove an average of 56±2% of the contaminants. In an HL-60 II culture contaminated with yeast, the ATPS treatment removed 50±1% of the contaminants. Finally, in a culture of HeLa cells contaminated with yeast, ATPS treatment removed 32±1% of the contaminant. These results indicate that the disclosed ATPS, while unable to fully decontaminate the culture, is currently able to substantially enrich the contaminated cell suspensions for the desired mammalian cells.

Each of these embodiments and obvious variations thereof is contemplated as falling within the spirit and scope of the claimed invention, which is set forth in the following claims. Moreover, the present concepts expressly include any and all combinations and sub-combinations of the preceding elements and aspects.

What is claimed is:

1. A method for separating contaminants from mammalian cells in an aqueous multiphase system, the method comprising:
    loading a container with a liquid having a top liquid phase and a bottom liquid phase, the top liquid phase being separated from the bottom liquid phase at a liquid-to-liquid interface, the top liquid phase having a top liquid density that is different than a bottom liquid density of the bottom liquid phase, the container having a top open end and a bottom closed end;
    inserting a cover medium in the container, the cover medium including a mixture of cultured mammalian cells and contaminants, the mixture remaining initially in a mixed form during a first time period, the cultured mammalian cells having a cell density and the contaminants having a contaminant density, the cell density being different than the contaminant density;
    centrifuging the container with the liquid, after the cover medium is inserted, during a second time period subsequent to the first time period; and
    in response to the centrifuging and in accordance with the cell density and the contaminant density, separating the cultured mammalian cells from the contaminants, the cultured mammalian cells being located at the liquid-to-liquid interface between the top liquid phase and the bottom liquid phase, the contaminants being located at the bottom closed end of the container.

2. The method of claim 1, further comprising forming, prior to the loading of the container, the top liquid phase and the bottom liquid phase in response to adding a mixture of polymers and salts to the liquid.

3. The method of claim 1, further comprising forming, prior to inserting the cover medium in the container, at least one intermediate liquid phase between the top liquid phase and the bottom liquid phase, the intermediate liquid phase having an intermediate liquid density that is different than the top liquid density or the bottom liquid density.

4. The method of claim 1, wherein the cell density is greater than the top liquid density and less than the bottom liquid density.

5. The method of claim 1, wherein the contaminant density is greater than the top liquid density, the bottom liquid density, and the cell density.

6. The method of claim 1, further comprising collecting the cultured mammalian cells from the liquid-to-liquid interface.

7. A method for separating contaminants from mammalian cells in an aqueous multiphase system, the method comprising:
    loading a liquid in a tube;
    in response to adding a mixture selected from a group consisting of at least one polymer and at least one salt, forming a multiphase liquid having a first phase and a second phase, each phase of the multiphase liquid having a respective and distinct phase density including a first density of the first phase and a second density of the second phase;
    adding a culture of mammalian cells mixed with contaminants in the multiphase liquid, the mammalian cells having a cell density that is greater than the first density but less than the second density, the contaminants having a contaminant density that is greater than the cell density and the second density;

subsequent to an initial time period, inserting the tube into a centrifuge;

centrifuging the tube for a predetermined time period; and in response to the centrifuging, accumulating the mammalian cells between the first phase and the second phase and sedimenting the contaminants at a bottom of the tube.

8. The method of claim 7, wherein the first phase is a top phase located near a top end of the tube, the second phase being a bottom phase located near the bottom of the tube.

9. The method of claim 7, further comprising forming an intermediate liquid phase between the first phase and the second phase, the intermediate liquid phase having an intermediate liquid density that is different than the first density of the first phase and the second density of the second phase.

10. The method of claim 7, further comprising moving a cover of the tube between a closed position in which a top open end of the tube is covered and an open position in which the top open end is uncovered, the cover being attached to the top open end of the tube.

\* \* \* \* \*